(12) United States Patent
Tsuchiya

(10) Patent No.: US 9,797,846 B2
(45) Date of Patent: Oct. 24, 2017

(54) INSPECTION METHOD AND TEMPLATE

(71) Applicant: NuFlare Technology, Inc., Yokohama (JP)

(72) Inventor: Hideo Tsuchiya, Tokyo (JP)

(73) Assignee: NuFlare Technology, Inc., Yokohama (JP)

( * ) Notice: Subject to any disclaimer, the term of this patent is extended or adjusted under 35 U.S.C. 154(b) by 0 days.

(21) Appl. No.: 15/096,313

(22) Filed: Apr. 12, 2016

(65) Prior Publication Data

US 2016/0305892 A1    Oct. 20, 2016

(30) Foreign Application Priority Data

Apr. 17, 2015 (JP) ................................. 2015-084794
Jun. 15, 2015 (JP) ................................. 2015-120548

(51) Int. Cl.
*G01N 21/00* (2006.01)
*G01N 21/956* (2006.01)
(Continued)

(52) U.S. Cl.
CPC ....... *G01N 21/956* (2013.01); *G01N 21/9501* (2013.01); *G06T 7/001* (2013.01);
(Continued)

(58) Field of Classification Search
CPC ............ G01N 21/9501; G01N 21/956; G01N 21/95607; G01N 2021/95615;
(Continued)

(56) References Cited

U.S. PATENT DOCUMENTS 7,564,545 B2 * 7/2009 Stokowski ............ G03F 7/705
356/237.5
2004/0021866 A1    2/2004 Watts et al.
(Continued)

FOREIGN PATENT DOCUMENTS

JP    2006-516065    6/2006
JP    2010-073703 A    4/2010
(Continued)

OTHER PUBLICATIONS

Korean Office Action dated Jun. 19, 2017, issued in Korean Patent Application No. 10-2016-0046946.

*Primary Examiner* — Michael P Stafira
(74) *Attorney, Agent, or Firm* — Oblon, McClelland, Maier & Neustadt, L.L.P.

(57) ABSTRACT

An inspection method for inspecting a substrate by using an optical image obtained by irradiating the substrate with light from a light source through an optical unit, and causing the light reflected by the substrate to be incident to a sensor, includes adjusting a focus offset value such that a focal distance for setting the signal-to-noise ratio of a programmed defect to the maximum level, is obtained by acquiring the optical image while changing a focal distance between the surface in which a first pattern is provided and the optical unit. The substrate includes the first pattern, a second pattern on the same plane as the first pattern, the programmed defect in the second pattern, and a third pattern on the same plane as the first pattern. The existence of a defect is detected by acquiring the optical image of the first pattern after the focus offset is adjusted.

19 Claims, 25 Drawing Sheets

(51) Int. Cl.
*G06T 7/00* (2017.01)
*G01N 21/95* (2006.01)

(52) U.S. Cl.
CPC .............. *G01N 2021/95676* (2013.01); *G01N 2201/067* (2013.01); *G06T 2207/10148* (2013.01); *G06T 2207/30148* (2013.01)

(58) Field of Classification Search
CPC ..... G01N 2021/95676; G01N 21/8806; G01N 21/21; G01N 2021/8825; G01N 21/9505; G01N 21/94; G01N 2201/06113; G01N 2021/151; G01N 2021/882
See application file for complete search history.

(56) References Cited

U.S. PATENT DOCUMENTS

| | | | |
|---|---|---|---|
| 2007/0229814 A1* | 10/2007 | Yamaguchi | G03F 1/84 356/237.4 |
| 2009/0026657 A1 | 1/2009 | Nimmakayala et al. | |
| 2015/0332452 A1 | 11/2015 | Tsuchiya et al. | |

FOREIGN PATENT DOCUMENTS

| | | |
|---|---|---|
| JP | 2010-534406 | 11/2010 |
| JP | 2012-26977 | 2/2012 |
| JP | 2014-0165203 A1 | 9/2014 |
| JP | 2015-232549 | 12/2015 |
| KR | 10-2006-0060265 | 6/2006 |

* cited by examiner

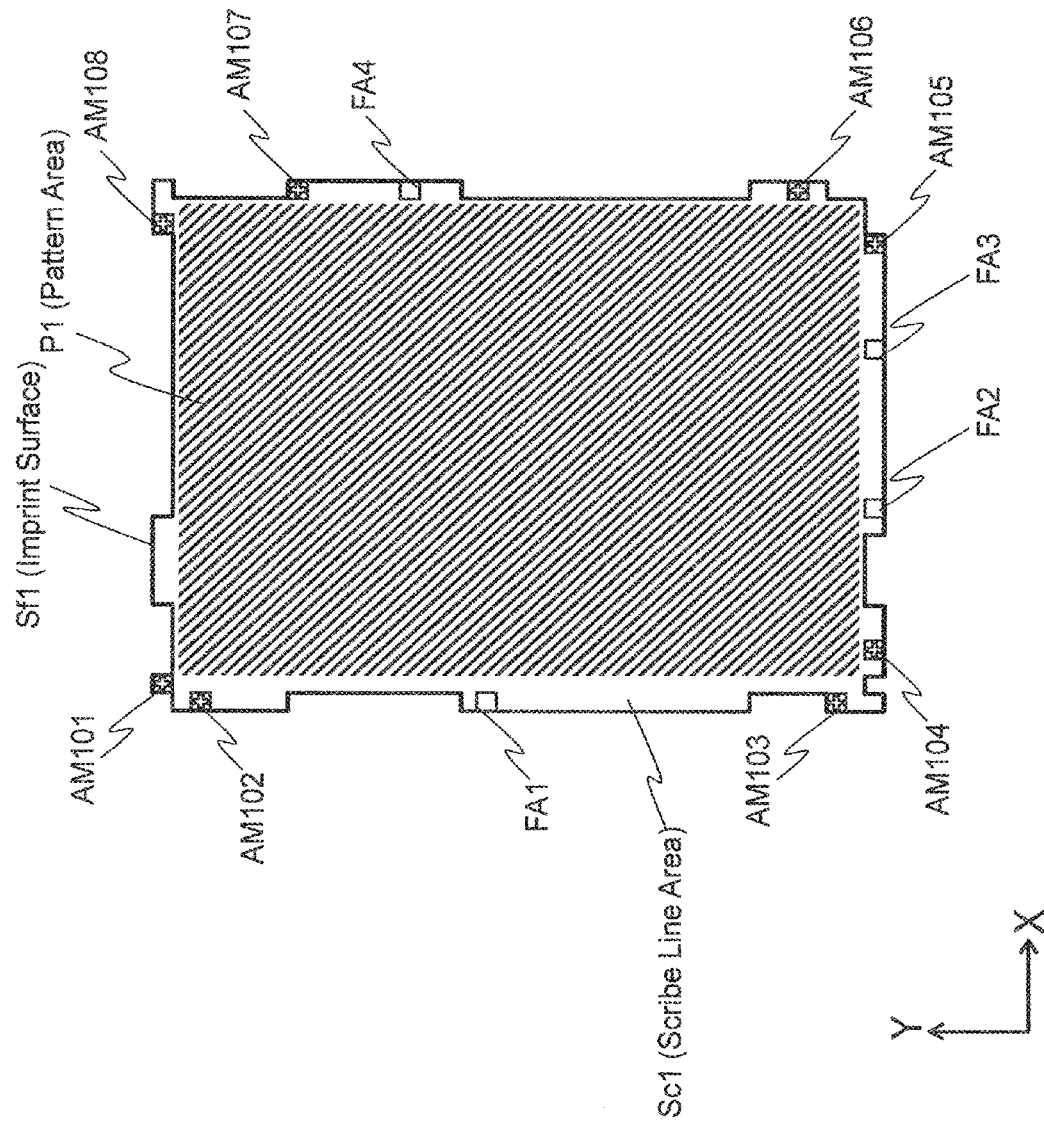

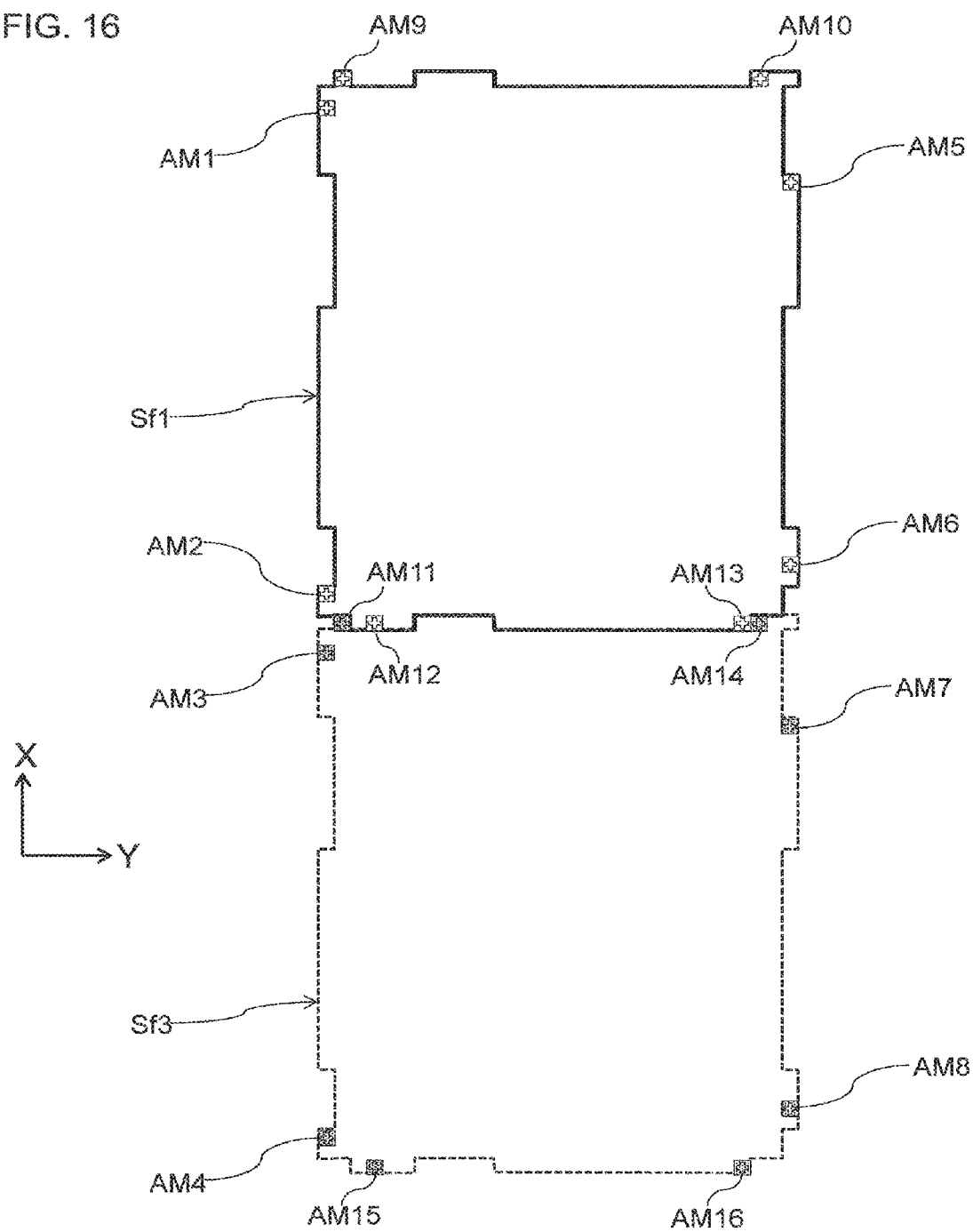

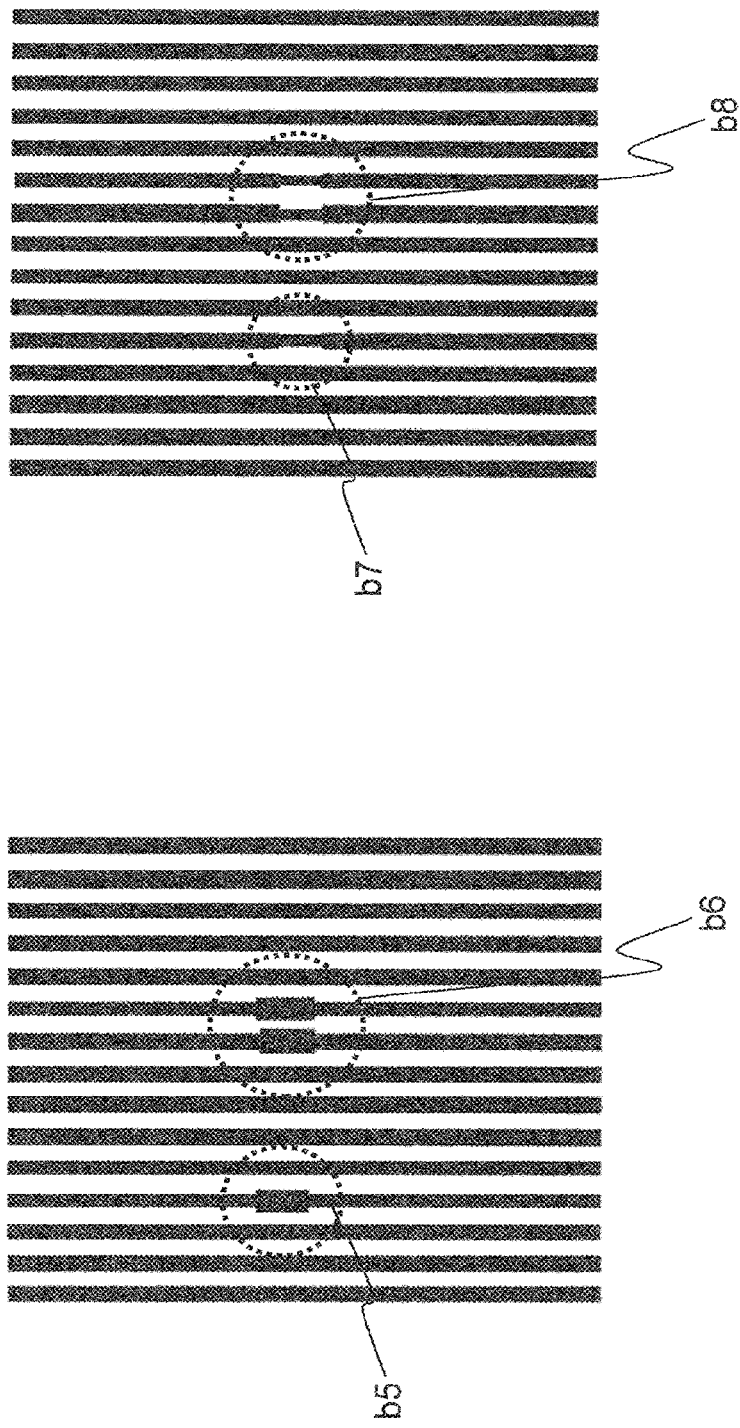

INSPECTION METHOD AND TEMPLATE

CROSS-REFERENCE TO THE RELATED APPLICATION

The entire disclosures of the Japanese Patent Applications No. 2015-84794, filed on Apr. 17, 2015 and No. 2015-120548, filed on Jun. 15, 2015 including specification, claims, drawings, and summary, on which the Convention priority of the present application is based, are incorporated herein in its entirety.

FIELD OF THE INVENTION

The present invention relates to an Inspection Method and a Template.

BACKGROUND

Recently, with an increasing integration degree of a semiconductor device, the dimensions of individual elements have become finer, and the widths of wiring and gate constituting each element have also become finer.

EUV (Extreme Ultraviolet) lithography and nanoimprint lithography (NIL) have attracted attention as technologies for forming fine patterns on a semiconductor wafer. Since the EUV lithography uses extreme ultraviolet light as a light source to transfer patterns of EUV mask onto the wafer, it is possible to form finer patterns on the wafer than a conventional exposure apparatus using ArF light. In the nanoimprint lithography, a fine pattern is formed in a resist by pressuring a template having a nanometer-scale fine structure to the resist on the wafer. In both the EUV lithography and the nanoimprint lithography, a pattern formed in the EUV mask and the template being an original plate is finer when compared with conventional ArF lithography. Thus, high inspection accuracy is required for the inspection thereof.

An exposure apparatus called a stepper or a scanner is used in the transfer process in the EUV lithography. In the exposure apparatus, light is used as a transfer light source, and a circuit pattern on the mask is projected onto the wafer while reduced from about one-fourth to about one-fifth size. Accordingly, the dimension of a circuit pattern to be formed in the mask is about four times to five times as large as a dimension of a circuit pattern on the wafer. On the other hand, in a template used in the nanoimprint lithography, a circuit pattern, having the same dimension as a circuit, is formed by digging a printing plate down to a predetermined depth. In a contemporary semiconductor device, a line width of a pattern or a width of a space between patterns might be ten nanometers to several tens of nanometers, and a depth of a dugout portion might be several tens of nanometers to one hundred nanometers.

Because the pattern of the template has the dimension identical to the dimension of the circuit, the defect existing in the template has a larger influence on the pattern imprinted to the wafer compared with the pattern of the mask. Because the template is used in the imprinting process a plurality of times, the defect is wholly imprinted to the wafer together with the pattern. Accordingly, in inspecting the pattern of the template, higher accuracy is required compared with the inspection of the pattern of the mask. For example, JP 2012-26977 A discloses an inspection apparatus for detecting the defect of the template.

The pattern formed in the template cannot be resolved in the case where the pattern is finer than a wavelength of a light source in an inspection apparatus. Generally the limitation of the dimension of the pattern that can be resolved, is known as a Rayleigh resolution limit. Nowadays, as microfabrication of the pattern of the circuit is progressed, it is possible that the dimension of a pattern becomes finer than the resolution limit of an optical system in an inspection apparatus.

Assuming that NA is a numerical aperture of an optical system in an inspection apparatus and that $\lambda$ is a wavelength of the light source, the resolution limit of the optical system is expressed by the formula (1). The numerical aperture NA is usually in the range of approximately 0.7 to approximately 0.8. Further, k1 is a coefficient depending on an image forming condition, and is in the range of approximately 0.5 to approximately 1.

$$R = k_1 (\lambda/NA) \quad (1)$$

In a contemporary semiconductor device manufacturing process, in inspecting the mask used in a reduced projection exposure of the circuit pattern to the wafer, the mask is irradiated with continuous light, having a wavelength of approximately 200 nm, close to the wavelength of the light source of the exposure apparatus. The light transmitted through or reflected by the mask is received by a sensor through a proper magnification optical system to obtain an electrical signal constituting an optical image of the mask. The dimension of the pattern formed in the mask is approximately four times as large as the line width (several tens of nanometers) of the pattern to be formed on the wafer, namely, approximately one hundred nanometers to several hundred nanometers.

In the formula (1), when the wavelength of the light source is set to 200 nm, and when the numerical aperture is set to 0.7, a formula (2) is obtained.

$$R = 0.5 \times (200/0.7) = 143 \text{ (nm)} \quad (2)$$

According to the formula (2), the resolution limit size in this case is 143 nm. That is, when the patterns of the mask come closer than 143 nm to each other, an electrical signal of a brightness amplitude corresponding to the pattern is not obtained by the sensor. This is similar for a pattern of a template. Because the pattern of the template has the same dimension as the circuit to be formed on the wafer, the pattern of the template cannot be resolved in principle. The shapes of some of the non-repetitive, slightly thick patterns such as a lead wire or a gate wire can occasionally be distinguished.

Instead of the inspection optical system provided with the above-mentioned light source, a method for acquiring a pattern by applying an electron beam or an atomic force is conceivable as a method for resolving the fine pattern to identify the defect. However, for the inspection in which the electron beam or the atomic force is used, there is a problem in that the inspection is not suitable for mass production of semiconductor device because of low throughput.

In the template in which a repetitive pattern finer than the resolution limit of the optical system in the inspection apparatus is formed, when a reflection optical image of the template is acquired, the optical image (electrical signal image) has brightness corresponding to a film quality of the template at a location where the pattern is not arranged. For example, the optical image becomes an even brightness close to a white level determined by calibration. At a location where the pattern is arranged, the optical image has the brightness different from that at the location where the pattern is not arranged, for example, the optical image is observed as an even gray image, that is, between the white level and a black level in the brightness.

On the other hand, when the defect exists at the location where a predetermined pattern is periodically formed, the periodicity of the pattern is disturbed, and the optical image becomes an image in which the brightness is changed according to a degree of the defect in the even gray image. For example, the brightness change is observed as an isolated white or black point.

The defect can be detected in the pattern finer than the resolution limit of the optical system by detecting the brightness change caused by the disturbance of the periodicity. Specifically, in the identical template, the defect is detected by using a die-to-die comparison method in which optical images of a plurality of dies are compared to each other or a cell comparison method in which optical images in the areas where the identical pattern is formed are compared to each other. For example, the two dies, which both appear to be the even gray image when the patterns have no defects, are compared to each other to determine that the image having the brightness change caused by the disturbance of the periodicity has the defect.

When the optical image is captured while a focal position between the pattern and the optical system is changed for the repetitive pattern finer than the resolution limit of the optical system, the brightness change, namely, a variation in gradation value is observed in each optical image. The variation in gradation value depends on the focal position. The focal position where the variation becomes the maximum is the position where the contrast of the optical image is maximized, namely, a focusing position. However, it is well known that a signal-to-noise (S/N) ratio of the defect inspection is occasionally improved when the defect is inspected while a given distance (focus offset) is intentionally provided with respect to the focusing position. Therefore, the focusing position where the contrast of the optical image becomes the maximum is obtained, and the inspection is performed using the position where the focusing position is corrected by the focus offset as the optimum focal position.

The focus offset also has an optimum value, and the optimum value depends on a type, a shape, and a dimension of the defect.

For example, it is considered that a line-and-space pattern is regularly arrayed with given periodicity. Assuming that the broken pattern defect is generated in the line-and-space pattern by disconnection, the defect is seen as a white bright spot in the even gray image when the defect is observed with the focus offset. At this point, when the focus offset is changed, the defect is seen as a black spot in the even gray image. In intermediate focus offset, amplitude of a defect signal cannot be obtained by an image sensor, and therefore the defect cannot be observed.

For example, when the defect, in which the adjacent line patterns are partially connected to each other to form a pattern bridge defect, exists in the line-and-space pattern, the pattern bridge defect caused by the short-circuit is seen as a black-and-white inversion of the broken pattern defect caused by the disconnection. That is, when the focus offset seen as the white bright spot in the broken pattern defect caused by the disconnection is applied to the pattern bridge defect caused by the short-circuit, the pattern bridge defect caused by the short-circuit is seen as the black spot while the black-and-white inversion of the broken pattern defect caused by the disconnection is generated. In the focus offset seen as the black spot in the broken pattern defect caused by the disconnection, the pattern bridge defect caused by the short-circuit is seen as the white bright spot.

In the above example, when the shape or dimension of the pattern bridge defect or broken pattern defect varies, the brightness of the defect, namely, the brightness of the white or black spot changes, or the focus offset in which the brightness becomes the maximum changes.

Therefore, in inspecting the template, the defect is detected by performing a preliminary inspection, the focus offset is adjusted using the defect, the optimum focus offset is found in order to detect the defect, and the inspection is performed. However, the focus offset cannot be adjusted when the defect is not detected in the preliminary inspection. For this reason, when the defect is not detected in the subsequent inspection, it is not distinguished whether the defect is not detected due to the actual absence of the defect or the improper focus offset, which results in a problem in that inspection quality cannot be guaranteed.

The present invention has been devised to solve the problem described above. An object of the present invention is to provide an inspection method for properly adjusting the focus offset to be able to accurately detect the defect of the pattern finer than the resolution limit of the optical system in the inspection apparatus.

Another object of the present invention is to provide an inspection method that can accurately detect the existence of a defect of a pattern finer than a resolution limit of an optical system of an inspection apparatus, by appropriately adjusting a focus offset, and reducing the influence of noise.

Further, another object of the present invention is to provide a template that can accurately detect the existence of a defect of a pattern finer than the resolution limit of an optical system of the inspection apparatus by accurately adjusting the focus offset.

Other advantages and challenges of the present invention are apparent from the following description.

SUMMARY OF THE INVENTION

According to one aspect of the present invention, an inspection method for inspecting a substrate to detect the existence of a defect using an optical image obtained by irradiating a substrate with light emitted from a light source through an optical unit, and causing the light reflected by the substrate to be incident to a sensor through the optical unit includes adjusting a focus offset value such that a focal distance for setting the signal-to-noise (S/N) ratio of a programmed defect to the maximum level, is obtained in an optical image of the programmed defect by acquiring the optical image while changing a focal distance between the surface in which a first pattern is provided and the optical unit. The substrate includes the first pattern consisting of a repetitive pattern that is finer than the resolution limit of the optical unit; a second pattern arranged on the same plane as the first pattern, having the same direction as the first pattern, and consisting of a repetitive pattern that is finer than the resolution limit of the optical unit; a programmed defect disposed in the second pattern, finer than the resolution limit of the optical unit; and a third pattern arranged on the same plane as the first pattern, having a shape reflecting the direction of the first pattern, not finer than the resolution limit of the optical unit. The existence of a defect of the first pattern is detected by acquiring an optical image of the first pattern after the focus offset is adjusted.

According to another aspect of the present invention, in an inspection method for inspecting a substrate to detect the existence of a defect using an optical image obtained by irradiating a substrate with light emitted from a light source through an optical unit, and causing the light reflected by the substrate to be incident to a sensor through the optical unit, the substrate includes a first pattern consisting of a repetitive pattern finer than the resolution limit of the optical unit; a second pattern arranged on the same plane as the first pattern, having the same direction as the first pattern, and consisting of a repetitive pattern finer than the resolution limit of the optical unit; a programmed defect disposed in the second pattern, finer than the resolution limit of the optical unit; and a third pattern arranged on the same plane as the first pattern, having a shape reflecting the direction of the first pattern, not finer than the resolution limit of the optical unit. The first pattern and the second pattern are a line-and-space pattern. The programmed defect includes at least one of a pattern bridge defect in which lines are short-circuited with each other, a broken pattern defect in which the line is disconnected, and a defect caused by an edge roughness. The optical unit includes a polarization beam splitter, a half-wavelength plate, a Faraday rotator, and an objective lens, and is configured to acquire an optical image of the programmed defect, after a focus offset value is adjusted, emitting light from the light source, reflecting the light by the polarization beamsplitter, transmitting the light through the half-wavelength plate, the Faraday rotator, the objective lens, irradiating the substrate with the light having a polarization plane of an angle except an angle within a range of an angle equal to or larger than −5 degrees and an angle equal to or smaller than 5 degrees, and a range of an angle equal to or larger than 85 degrees and an angle equal to or smaller than 95 degrees with respect to a repetitive direction of a repetitive pattern of the first pattern, transmitting the light reflected by the substrate through the objective lens, the half-wavelength plate, the Faraday rotator, and the polarization beamsplitter, causing the light to be incident to the sensor. The inspection method includes setting a condition range of a focus offset value for adjusting the focus offset value. A condition range of an angle of the Faraday rotator is set for adjusting an angle with respect to the repetitive direction of the repetitive pattern of the first pattern. An optical image of the programmed defect is acquired under a plurality of conditions within the range of the condition range of a focus offset value while changing the condition of the focus offset value, and changing the condition of the angle of the Faraday rotator within the condition range of an angle of the Faraday rotator. The plurality of optical images are analyzed, and then an evaluation scale is calculated by dividing a signal intensity of either the pattern bridge defect or the broken pattern defect of the programmed defect by a signal intensity of noise caused by the edge roughness. The condition of the focus offset value and the condition of an angle of the Faraday rotator are extracted for acquiring an optical image of the programmed defect using the evaluation scale, and then the inspection condition of the focus offset value and the inspection condition of the angle of the Faraday rotator are determined for detecting the existence of a defect of the first pattern. An optical image of the first pattern is acquired according to the inspection condition of the focus offset value and the inspection condition of the angle of the Faraday rotator, and then the existence of a defect of the first pattern is detected.

According to another aspect of the present invention, a template includes an imprint surface. A pattern area in which a first pattern is disposed, and a scribe line area, surrounding the first pattern, are disposed in the imprint surface. The scribe line area includes an alignment mark area in which an alignment mark is arranged, a second pattern and a third pattern disposed in any area of the scribe line area except the alignment mark area, and a programmed defect disposed in the second pattern. The first pattern consists of a repetitive pattern finer than the resolution limit of an optical unit of an inspection apparatus for detecting the existence of a defect of the first pattern by acquiring an optical image of the first pattern. The second pattern has the same direction as the first pattern, and consists of a repetitive pattern finer than the resolution limit of the optical unit. The programmed defect is finer than the resolution limit of the optical unit. The third pattern has a shape reflecting the direction of the first pattern, not finer than the resolution limit of the optical unit.

According to another aspect of the present invention, a template includes an imprint surface. A pattern area in which a first pattern is disposed, and a scribe line area, surrounding the first pattern are disposed in the imprint surface. The scribe line area includes an alignment mark area. The alignment mark area includes a second pattern, a programmed defect, and an area in which the second pattern is not disposed. The second pattern has the same direction as the first pattern, and consists of a repetitive pattern finer than the resolution limit of an optical unit of an inspection apparatus for detecting the existence of a defect of the first pattern by acquiring an optical image of the first pattern. The programmed defect is disposed in the second pattern, and is finer than the resolution limit of the optical unit. The area in which the second pattern is not disposed, forms the alignment mark by the difference of the contrast between the area in which the second pattern is not disposed, and the area in which the second pattern is disposed. The alignment mark has a shape reflecting the direction of the first pattern, not finer than the resolution limit of the optical unit.

BRIEF DESCRIPTION OF THE DRAWINGS

A more complete appreciation of the present invention and many of the advantages thereof will be readily obtained as the present invention becomes better understood by reference to the following detailed description when considered in connection with the accompanying drawings, wherein:

FIG. 5 is a view illustrating the alignment mark area and focus offset adjusting pattern area, provided on the imprint surface of the template;

FIG. 16 is a schematic plan view illustrating the imprint surface of the template according to the second embodiment;

FIG. 26 is an example of an isolated line width defect of the pattern, and an example of two neighboring line width defects of the pattern;

FIG. 27 is an example of an isolated line width defect of the pattern, and an example of two neighboring line width defects of the pattern;

DETAILED DESCRIPTION OF THE EMBODIMENT

Figure 1:
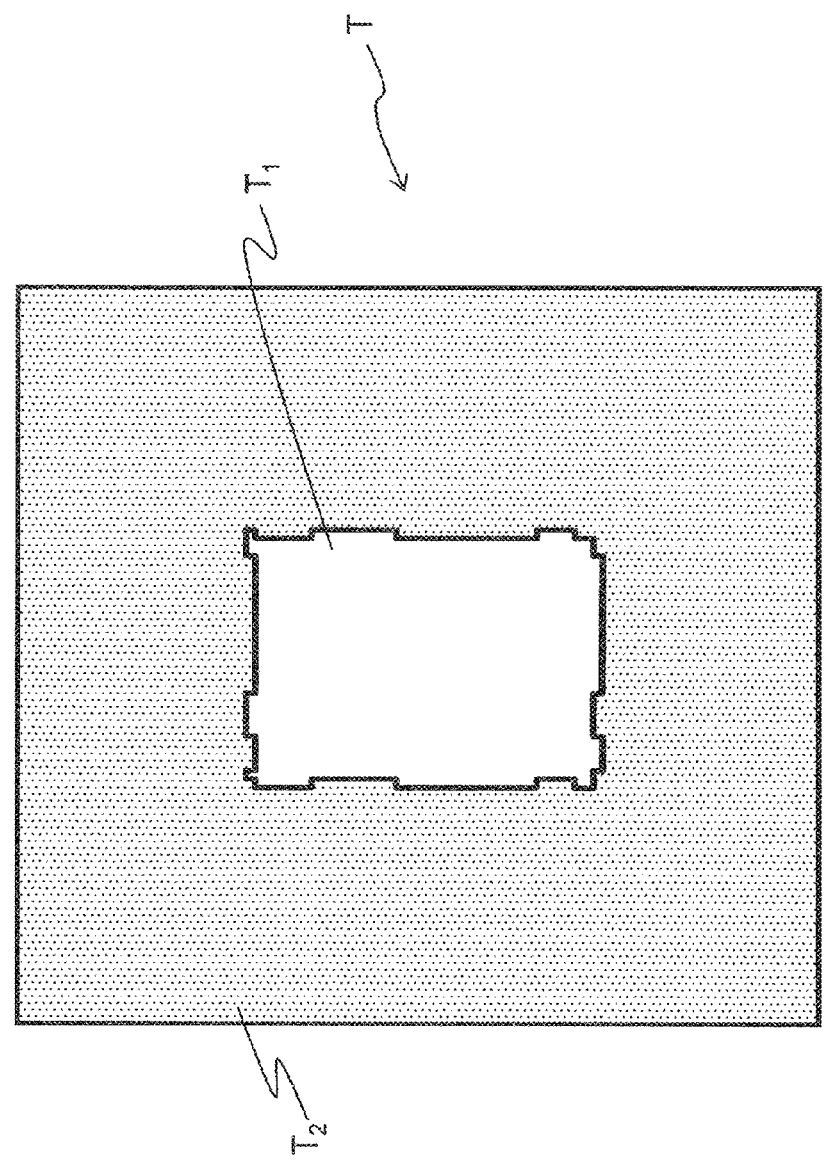
FIG. 1 is a plan view schematically illustrating the template positioned on the table of the inspection apparatus.

The embodiments will now be described with reference to the accompanying drawings, wherein the same reference numerals designate corresponding or identical elements throughout the various drawings.

As described above, according to the conventional method of inspecting the template, in which a repetitive pattern finer than the resolution limit of an optical system of an inspection apparatus is formed, the appropriate defect is detected by performing the preliminary inspection, and then the focus offset is adjusted using the defect. Next, the inspection is performed after the focus offset optimum for detecting a defect is determined. However, according to the conventional method, the focus offset cannot be adjusted in the case that the defect is not detected by the preliminary inspection.

Further, the optimum position of the focus offset depends on the repetitive direction of the inspection pattern as mentioned below. Accordingly, even if the focus offset is appropriately adjusted by the preliminary inspection, an optical image cannot be acquired at the optimum focus position when the direction of the repetitive pattern, during the adjustment of the focus offset, is different to the direction of the repetitive pattern during the acquisition of the optical image in the inspection. This problem will be described below.

The optical image of the repetitive pattern formed in the template, is sequentially acquired in every predetermined area while the table, which holds the template, is moved. For example, the area in which the repetitive pattern is formed is virtually divided into a plurality of stripe-shaped small areas. Each stripe aligned in the Y-direction has the same length as the total length of the inspection area in the X-direction. While the table is moved in the −X-direction, an optical image of one stripe-shaped small area is sequentially acquired in the X-direction. When the table reaches the end of one stripe-shaped small area, the table moves stepwise in the −Y-direction. Then, an optical image of the neighboring stripe-shaped small area in the Y-direction, is sequentially acquired in the −X-direction while the table moves in the X-direction. Optical images of all stripe-shaped small areas are acquired by repeating the above-mentioned process.

One example of a repetitive pattern formed in the template, is a line-and-space pattern of which a line pattern, having two edges extended in Y-direction, is repeated in the X-direction. As mentioned above, the direction of the movement of the table is parallel to the X-direction, and is also parallel to the direction where the pattern is repeated. In this case, the focus position corrected for the focus offset should be the optimum focus position.

The optimum value of the focus offset is obtained during the preliminary inspection, and is then used for the determination of the appropriate focus position during the inspection. However, even if the inspection pattern of the preliminary inspection is the same as the inspection pattern of the inspection, the optimum focus offset of the preliminary inspection becomes different to the optimum focus offset of the inspection when the direction of the pattern, while the optical image is acquired, that is, the direction where the pattern is repeated parallel to the direction of the movement of the table, is different between the preliminary inspection and the inspection. In the above-mentioned example, when two edges of the line pattern are extended in the X-direction, and the direction where the pattern is repeated is in the Y-direction, by rotating the template by 90 degrees, the optimum of the focus offset becomes different to the above-mentioned optimum focus offset. However, as the inspection pattern is finer than the resolution limit of the optical system of the inspection apparatus, it is impossible to know the direction in which the pattern is repeated differs between the preliminary inspection and the inspection. As a result, the optical image is not acquired at the optimum focus position.

In view of the above-mentioned problem, a programmed defect is formed in the template, and the focus offset is adjusted using the programmed defect according to the present embodiment. Thereby, the inspection can be performed at the optimum focus offset at any time regardless of whether or not the inspection pattern includes a defect.

Further, according to the present embodiment, the pattern having the shape reflecting the direction of the inspection pattern, and the dimension equal to or more than the resolution limit of the optical system of the inspection apparatus, is provided in the template. Thereby, it is possible to easily know the direction of the inspection pattern when the optimum focus offset is obtained. Therefore, the optical image can be acquired at the optimum focus position by matching the direction with the direction of the pattern while the optical image is acquired.

One example of the inspection pattern formed in the template is a first pattern consisting of a repetitive pattern finer than the resolution limit of the optical system of the inspection apparatus. Specifically, the first pattern is, for example, a repetitive pattern such as a line-and-space pattern or contact-hole pattern, consisting of a function element to be imprinted to a wafer via a resist film.

Further, in the present embodiment, a second pattern consisting of a repetitive pattern finer than the above-mentioned resolution limit is provided on the same surface as the first pattern in the template at the external peripheral part of the area where the first pattern is formed. The direction of the second pattern is the same as the direction of the first pattern. For example, in the case where the first pattern is a line-and-space pattern where a line pattern having two edges (the longer two sides of the four edges) extended in the Y-direction, is repeated in the X-direction, the second pattern is also a line-and-space pattern where a line pattern having two edges (the longer two sides of the four edges) extended in the Y-direction, is repeated in the X-direction. Further, in the case where the first pattern is a contact hole pattern of which the distance Wx between holes in the X-direction, is longer than the distance Wy between holes in the Y-direction, the second pattern is also a contact hole pattern of which the distance Wx between holes in the X-direction, is longer than the distance Wy between holes in the Y-direction.

A programmed defect, which is finer than the above-mentioned resolution limit, is provided in the second pattern. Further, a third pattern having the dimension equal to or more than the resolution limit of the optical system, and the shape reflecting the direction of the first pattern, is provided on the same surface as the first pattern at the external peripheral part of the area where the first pattern is formed.

Next, the present embodiment will be described below referring to the drawings.

In the first embodiment, the second pattern where the programmed defect is provided and the third pattern for detecting the direction of the inspection pattern are provided in a scribe line area except an alignment mark area in the imprint surface of the template.

In the second embodiment, the alignment mark area provided in the scribe line area, includes (1) the second pattern including the programmed defect, and (2) the area where the second pattern is not provided, for forming the alignment mark for performing an alignment using the difference of the contrast between the area where the second pattern is provided, and the area where the second pattern is not provided.

In the third embodiment, as in the first embodiment, the above-mentioned second pattern and third pattern are provided in the above-mentioned scribe line area, however the inspection method for inspecting a template using the second pattern and third pattern is different to the inspection method according to the first embodiment.

First Embodiment

The template of the first embodiment is one in which a circuit pattern is engraved in a glass substrate, and the template has a mesa structure in which a portion corresponding to an area necessary for the imprint is left in a convex shape while a surrounding area of the portion is removed by a digging process. FIG. 1 is a plan view schematically illustrating a state in which the template is arranged on a table of the inspection apparatus. In FIG. 1, the template is designated by the numeral T, the numeral $T_1$ corresponds to a convex portion, and the numeral $T_2$ corresponds to the dugout portion. The convex portion $T_1$ becomes the imprint surface.

The circuit pattern is formed on the imprint surface to be imprinted to the wafer. In the inspection of the template, the circuit pattern is the inspection pattern. The circuit pattern consists of a repetitive pattern such as a line-and-space pattern or contact hole pattern, that is, a regular repetitive pattern having periodicity.

Figure 2:
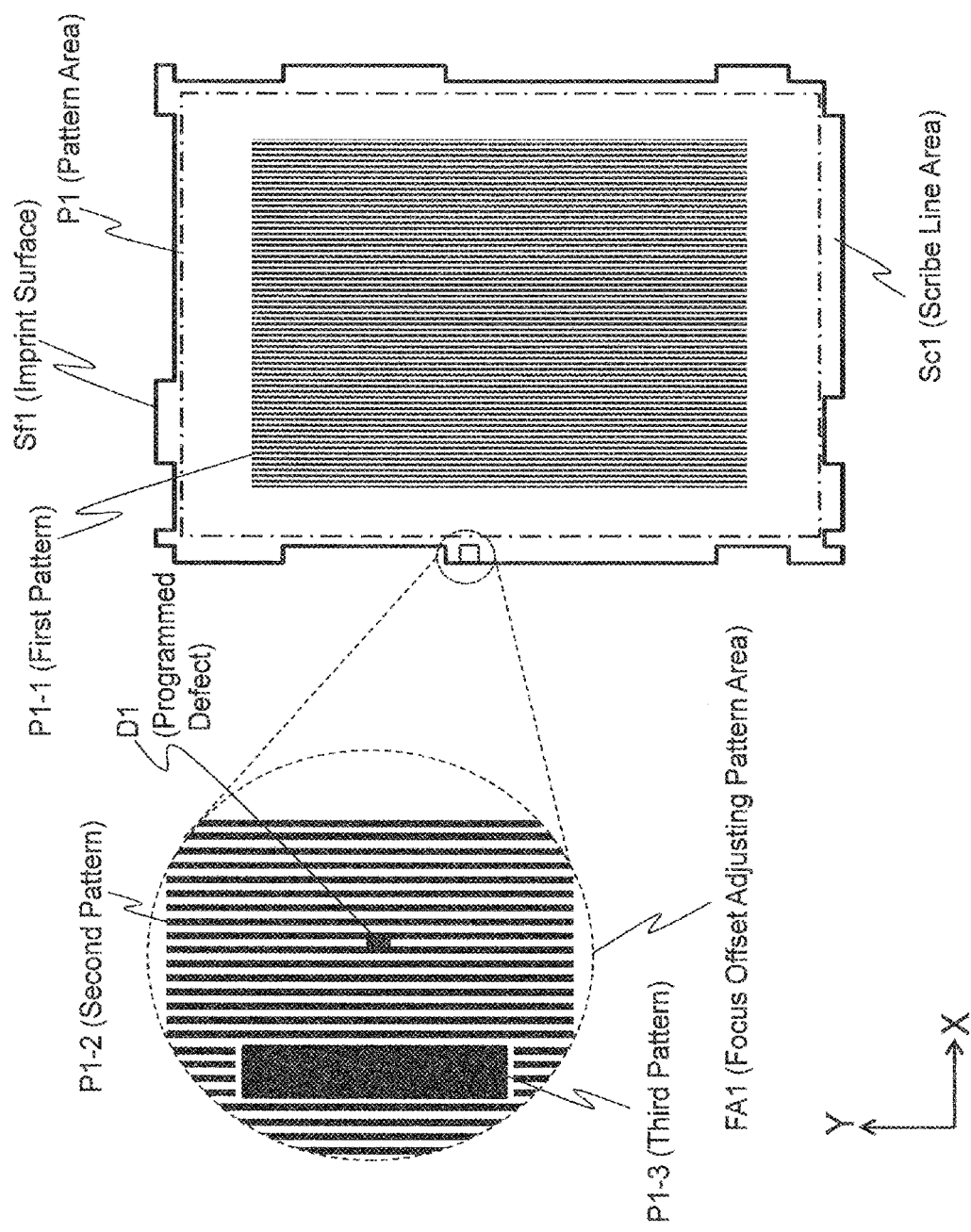
FIG. 2 is a view schematically illustrating a focus offset adjusting pattern area according to the first embodiment.

FIG. 2 is a schematic plan view of the imprint surface of the template according to the present embodiment. As shown in FIG. 2, in the imprint surface Sf1, the first pattern P1-1, the dimension of which is finer than the resolution limit of the optical system of the inspection apparatus, is formed in the pattern area P1 where the inspection pattern is provided. The first pattern P1-1 is a line-and-space pattern. In FIG. 2, two edges of the line pattern of the first pattern P1-1 are extended in the Y-direction, and the line pattern is repeated in the X-direction. A pattern, which is formed in a memory mat portion of a semiconductor chip, can be cited as an example of the first pattern P1-1. The first pattern P1-1 is formed by digging a glass substrate to a depth between 10 nm and 100 nm, for example. Another pattern having the dimension equal to or more than the resolution limit of the optical system in addition to the first pattern P1-1, may be formed in the pattern area P1.

Figure 3:
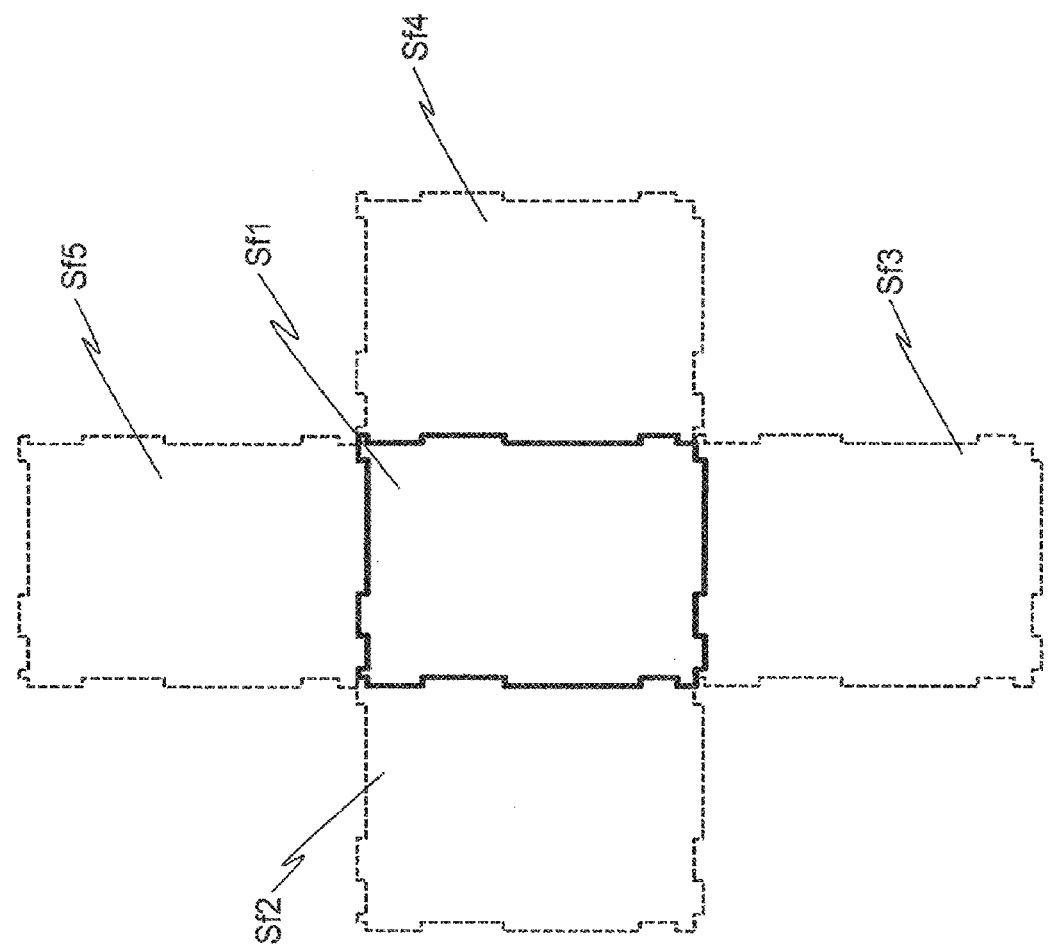
FIG. 3 is a view illustrating a relationship between an imprint surface of the template and a neighboring imprint surface of the template.

FIG. 3 is a view illustrating a relationship between an imprint surface Sf1 of the template shown in FIG. 2, and another imprint surface positioned around the imprint surface Sf1. In FIG. 3, areas (Sf2 to Sf5) indicated by dotted lines are other imprint surfaces that are imprinted to the surroundings of the imprint surface Sf1. As can be seen from FIG. 3, an outline of the imprint surface has a complex irregular shape. This is so the adjacent imprint surfaces interlock so as not to overlap each other.

Figure 4:
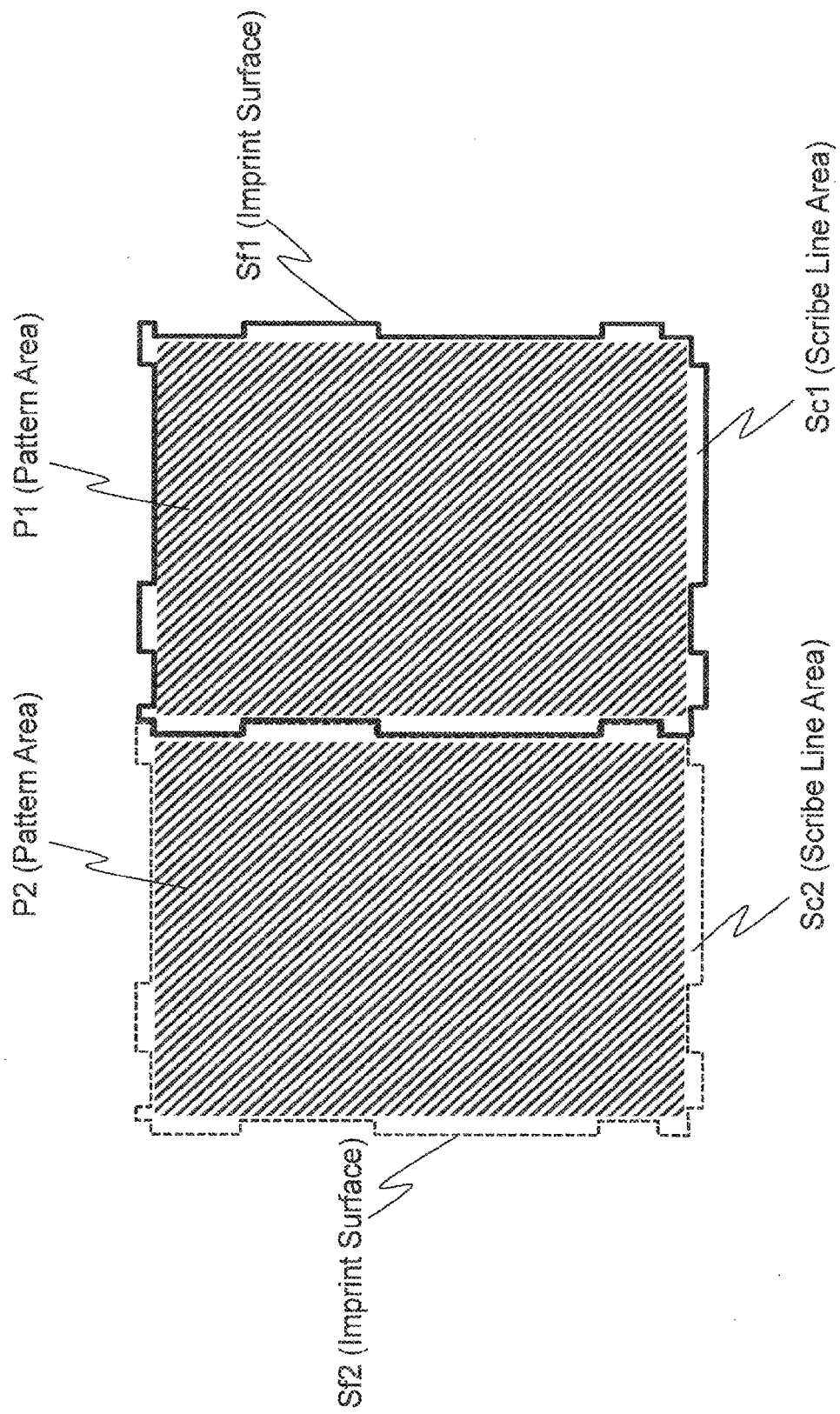
FIG. 4 is an expanded view of a part of FIG. 3.

FIG. 4 is an enlarged view of imprint surfaces Sf1 and Sf2 shown in FIG. 3. Scribe line areas Sc1 and Sc2 are positioned between the pattern areas P1, P2 and the outer peripheries of the imprint surfaces Sf1 and Sf2. The scribe line areas Sc1 and Sc2 are areas used as scribe lines, that is, to cut the chips in a final process of semiconductor manufacturing. The scribe line areas Sc1 and Sc2 are overlapping margin areas that are provided such that the pattern areas P1 and P2 do not overlap each other during the imprint. The widths of the scribe line areas Sc1 and Sc2 can be in a range of from approximately 50 μm to approximately 100 μm, for example.

According to the present embodiment, in FIG. 2, the focus offset adjusting pattern area FA1 is disposed in the scribe line area Sc1 provided in the outer circumferential part of the pattern area P1. In the focus offset adjusting pattern area FA1, a pattern following the first pattern P1-1, that is, a second pattern P1-2 equivalent to the shape and size of the first pattern P1-1, and having the same directivity as the first pattern P1-1, is provided. Specifically, the second pattern P1-2 is a line-and-space pattern having a dimension finer than the resolution limit of the optical system of the inspection apparatus, and having a shape of which two edges of the line pattern is extended in the Y-direction, and the line pattern is repeated in the X-direction, in the same manner as the first pattern P1-1. The second pattern P1-2 is formed by digging a glass substrate to a depth of between 10 nm and 100 nm, for example. Further, in FIG. 2 when the first pattern P1-1 is rotated 90 degrees, the pattern becomes the shape of which two edges of the line pattern is extended in the X-direction and the line pattern is repeated in the Y-direction. The second pattern P1-2 becomes the shape of which the two edges of the line pattern is extended in the X-direction and the line pattern is repeated in the Y-direction when the second pattern is rotated 90 degrees, in the same manner as the first pattern P1-1.

As shown in FIG. 2, the programmed defect D1 is disposed in the second pattern P1-2. The programmed defect D1 is also finer than the resolution limit of the optical system of the inspection apparatus, in the same manner as the first pattern and the second pattern.

Figure 7:
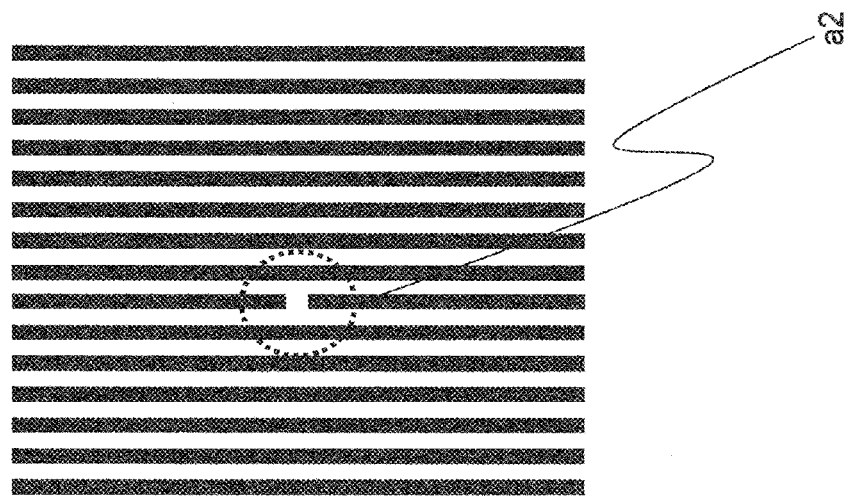
FIG. 7 is one example of a programmed broken pattern defect.
Figure 6:
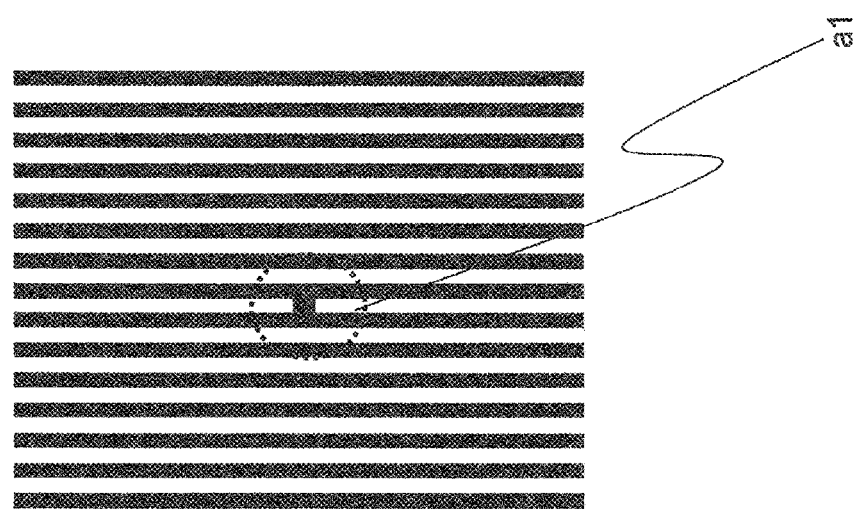
FIG. 6 is one example of a programmed pattern bridge defect.

An example of the programmed defect as mentioned in the present embodiment is shown in FIG. 6 and FIG. 7. In these drawings, according to the present embodiment, the background pattern of the programmed defect is the second pattern. The programmed defect in the area a1 in FIG. 6 is a pattern bridge defect, which is the same as the programmed defect d1 in FIG. 2. On the other hand, the programmed defect in the area a2 in FIG. 7 is a broken pattern defect.

The defect is not limited to examples as shown in FIG. 6 and FIG. 7. The programmed defect can be another type of defect, for example, a programmed defect different in dimension or shape. Further, a plurality of programmed defects, different in at least one of dimension, shape, and quantity, can be disposed.

The optimum value of the focus offset can be changed depending on the type, dimension, and shape of the defect. Therefore, by disposing a plurality of programmed defects, which are different to in type, dimension, and shape, the optimum focus offset of all defects can be detected.

For example, the dimension of the defect shown in FIG. 6 and FIG. 7 is the same size as the line width of the second pattern. However, the dimension of the defect can be approximately half the size or twice the size of the second pattern.

Further, the programmed defect is not limited to the broken pattern defect and the pattern bridge defect. The programmed defect can be simulated edge roughness, a defect of which the line width of the line pattern is wide at a specific location, or a defect of which the line width of the line pattern is thin at a specific location.

Further, more than two adjacent defects can be disposed. By disposing a plurality of the same type of defects having different sizes, the programmed defects can be used as an indication for determining whether the detection sensitivity for a defect of the inspection apparatus is fluctuated.

Figure 22:
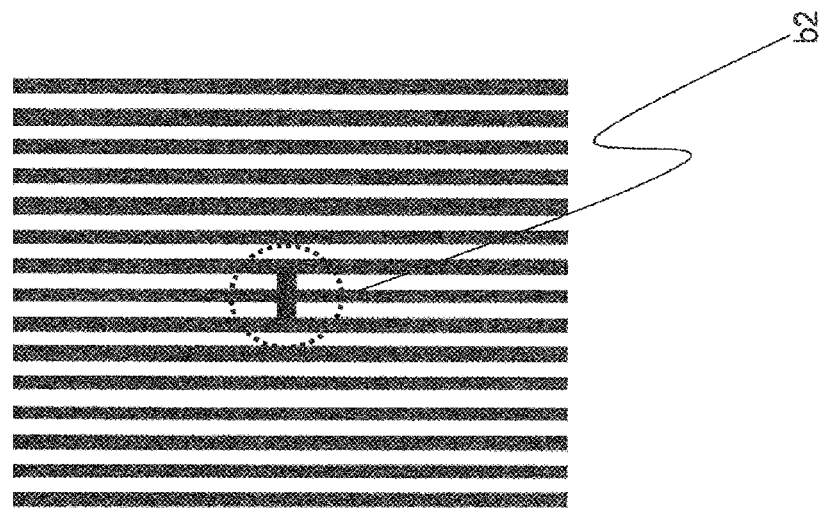
FIG. 22 is an example of three neighboring pattern bridge defects in a line.
Figure 23:
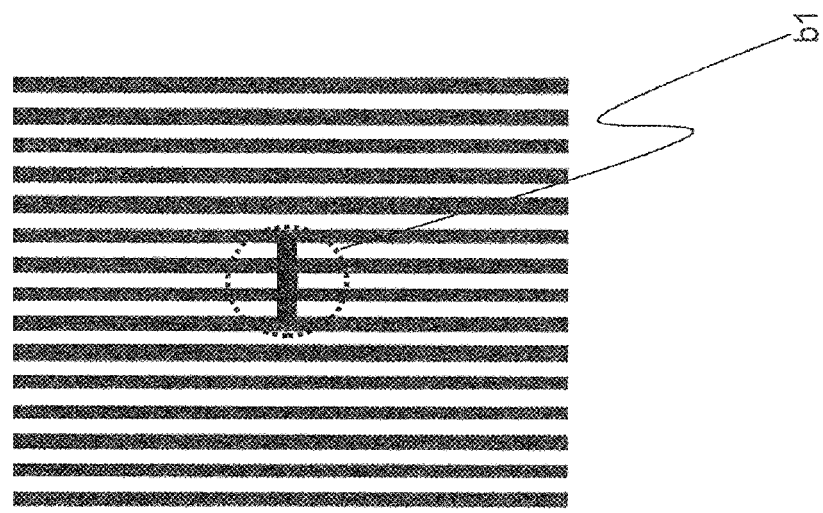
FIG. 23 is an example of two neighboring pattern bridge defects in a line.

For example, in the case where a signal of a programmed defect is fluctuated with time, depending on the dimension of the programmed defect while the optical image of the programmed defect is acquired by the inspection apparatus, it is preferable that the inspection process is suspended at the preliminary inspection stage before the inspection. As one example, although the inspection apparatus can detect all programmed defects at the beginning of the inspection, as the time for the inspection progresses the sensitivity for detecting a defect is fluctuated, as a result, the programmed defect of three neighboring pattern bridge defects as shown in the area b1 of FIG. 22, can be detected, however the programmed defect of two neighboring pattern bridge defects as shown in the area b2 of FIG. 23 cannot be detected. FIG. 22 is an example of three neighboring pattern bridge defects in a line. FIG. 23 is an example of two neighboring pattern bridge defects in a line. Causes for decreasing the sensitivity for detecting a defect may include, for example, a decrease in the light quantity of the light source or vibration of the table. Accordingly, in this case it is preferable that a series of inspection processes are suspended at the stage of the focus offset adjustment to find the cause of the problem of the inspection apparatus.

Other examples of the programmed defect which cannot be detected because of the fluctuation of the sensitivity of the inspection apparatus are illustrated in FIGS. 24 to 27.

Figure 25:
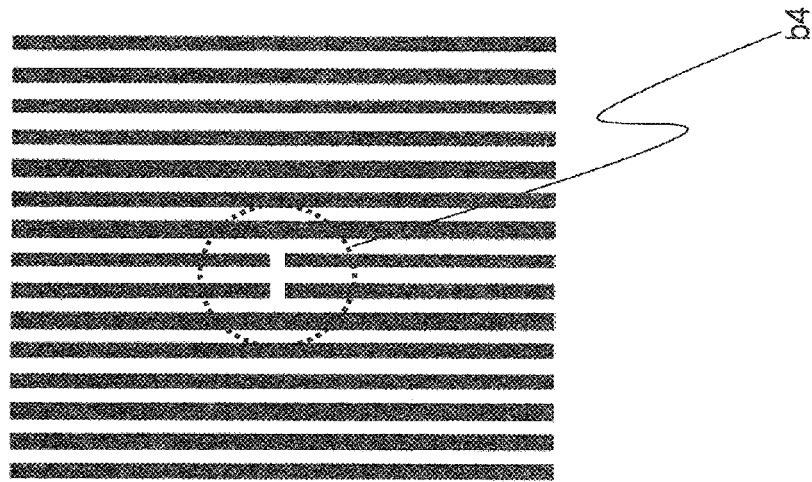
FIG. 25 is an example of two neighboring broken pattern defects in a line.
Figure 24:
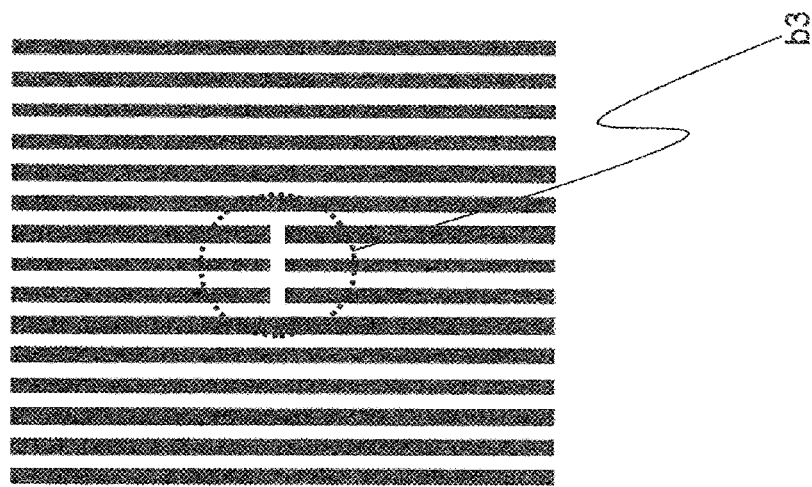
FIG. 24 is an example of three neighboring broken pattern defects in a line.

The area b3 of FIG. 24 illustrates one example of three neighboring pattern broken pattern defects in a line. The area b4 of FIG. 25 illustrates one example of two neighboring broken pattern defects in a line. Further, FIG. 26 illustrates an example of programmed defects of which the line width of the line pattern is locally thickened, and includes the case where an isolated defect is caused, as shown in the area b5, and the case where two neighboring defects are caused, as shown in the area b6. On the other hand, FIG. 27 illustrates an example of a programmed defect of which the line width of the line pattern is locally thinned, and the case where an isolated defect is caused, as shown in the area b7, and the case where two neighboring defects are caused, as shown in the area b8.

When the sensitivity of the detection of the inspection apparatus is decreased, the inspection apparatus can detect large defects as shown in the area b3 of FIG. 24, the area b6 of FIG. 26, and the area b8 of FIG. 27. However, the inspection apparatus cannot detect small defects as shown in the area b4 of FIG. 25, the area b5 of FIG. 26, and the area b7 of FIG. 27.

In FIG. 2, the third pattern P1-3, in addition to the second pattern P1-2, is disposed in the focus offset adjusting pattern area FA1. The third pattern is also formed by digging a glass substrate to a depth between 10 nm and 100 nm, for example.

The third pattern P1-3 has a dimension larger than the resolution limit of the optical system of the inspection apparatus, and two edges of the line pattern are extended in the same direction as the first pattern P1-1 and the second pattern P1-2, that is, in the Y-direction. Therefore, the inspection apparatus can easily detect the direction of the first pattern P1-1 as the inspection target if the inspection apparatus can detect the third pattern.

The shape of the third pattern P1-3 is not limited to the line pattern. The shape of the third pattern P1-3 can be any shape which can indicate the directivity of the first pattern P1-1 and the second pattern P1-2. For example, the shape may be a cross shape of which two lines having different widths or different lengths are combined to make a relationship between the width or length of the line, and the directivity of the first pattern P1-1 and the second pattern P1-2. For example, the line width of these lines can be between 2 μm and 10 μm, and the length of these lines can be between 10 μm and 50 μm.

For example, the length of two lines consisting of the cross shape is changed, thereby the direction of the longer line matches the direction in which the edge of the first pattern P1-1 and the edge of the second pattern P1-2 is extended. In this case, it is realized that the first pattern P1-1 and the second pattern P1-2 include the shape of which two edges of the line pattern are extended in the Y-direction, and the line pattern is repeated in the X-direction, if the longer line is parallel to the Y-direction of the table.

Further, the shape of the third pattern P1-3 maybe L-shaped, T-shaped, or F-shaped. In this case, an upright state can be distinguished with a state turned over 90 degrees. Accordingly, by relating either the upright state or the state turned over 90 degrees to the directivity of the first pattern P1-1 and the second pattern P1-2, the directivity of the first pattern P1-1 is easily obtained from the third pattern P1-3.

FIG. 5 is a view illustrating the alignment mark area and focus offset adjusting pattern area disposed on the imprint surface of the template. In FIG. 5, portions denoting the reference numerals are the same as in FIG. 2, and a repeated explanation is therefore omitted.

In FIG. 5, the alignment mark areas (AM101 to AM108), and the focus offset adjusting pattern areas (FA1 to FA4) are disposed in the scribe line area Sc1 in the outer periphery portion of the pattern area P1.

In the alignment mark areas (AM101 to AM108), the alignment mark used for performing alignment, for example, the adjustment of the position and rotation in the manufacturing process of the semiconductor integration circuit, is provided. The alignment mark areas are disposed in the scribe line area Sc1 at four corners (or an area around the four corners) of the imprint surface Sf1.

The focus offset adjusting pattern area FA1 has already been explained using FIG. 2. In FIG. 5, focus offset adjusting pattern areas (FA1 to FA4) are disposed on the imprint surface Sf1. The focus offset adjusting pattern areas (FA2 to FA4) include the same construction as the focus offset adjusting pattern area FA1. The area where these focus offset adjusting pattern areas (FA1 to FA4) are disposed are not limited to the four corners of the imprint surface Sf1 (and the area around the four corners), the area where these focus offset adjusting pattern areas are disposed may be anywhere in the scribe line area Sc1 with the exception of the alignment mark areas (AM101 to AM108).

According to the present embodiment the template includes the first pattern disposed on the imprint surface; the second pattern and the third pattern disposed in the alignment mark area at the outer periphery portion of the area where the first pattern is disposed and the outer periphery portion with the exception of the alignment mark area; and the programmed defect disposed in the second pattern. Accordingly, the inspection apparatus can appropriately adjust the focus offset, thereby accurately detecting the pattern defects finer than the resolution limit of the optical system of the inspection apparatus.

In the present embodiment, it is preferable that a plurality of focus offset adjusting pattern areas are disposed on the imprint surface of the template as shown in FIG. 5. Thereby, even if a part of the focus offset adjusting pattern areas is not appropriate for adjusting the focus offset as a result of a foreign particle such as dirt or dust, as one example, the inspection process can continue smoothly by using another focus offset adjusting pattern area.

Next, the inspection method for the template according to the present embodiment will be described.

Figure 8:
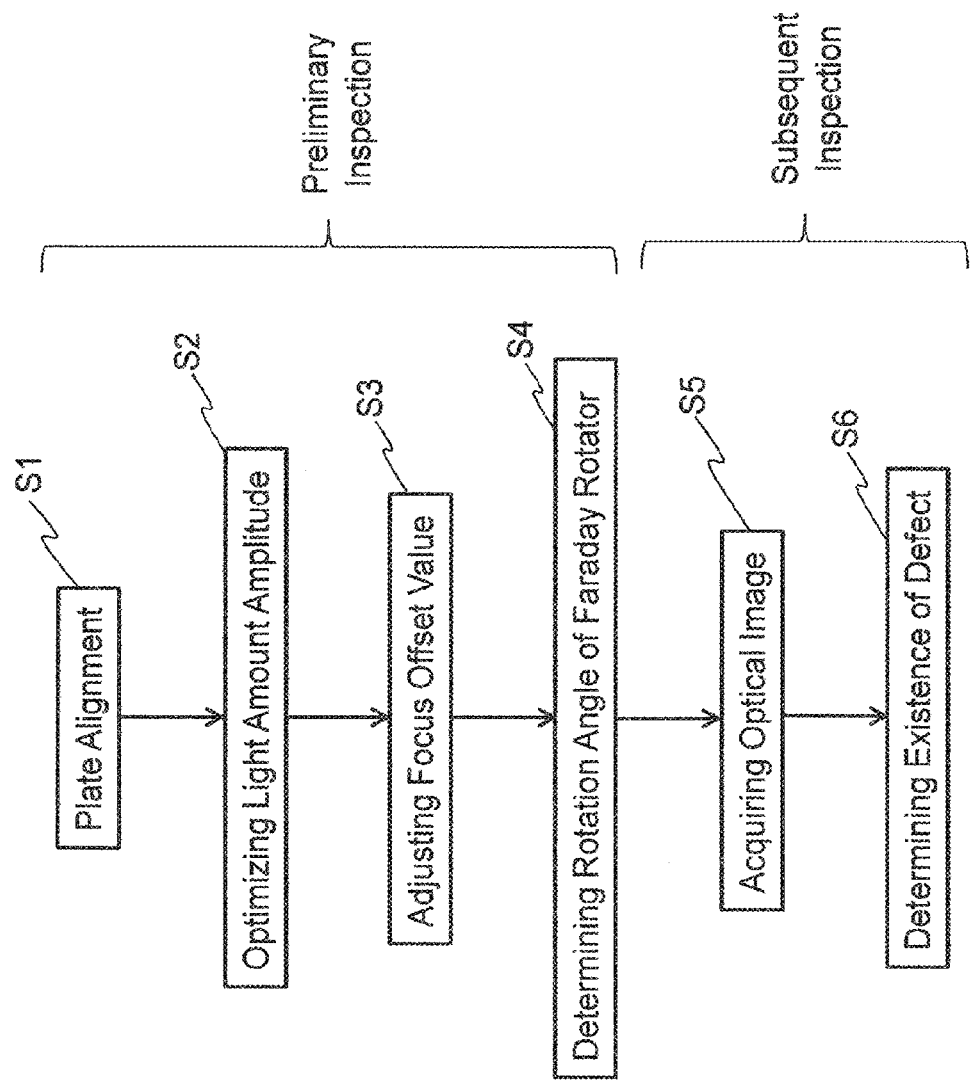
FIG. 8 is a flowchart illustrating the inspection method according to the first embodiment.

FIG. 8 is a flowchart illustrating the inspection method according to the present embodiment. In FIG. 8, the inspection process for determining the existence of a defect based on an optical image of the inspection target corresponds to S5 and S6, and S1 to S4 corresponds to the preliminary inspection process that is performed before the inspection.

Figure 9:
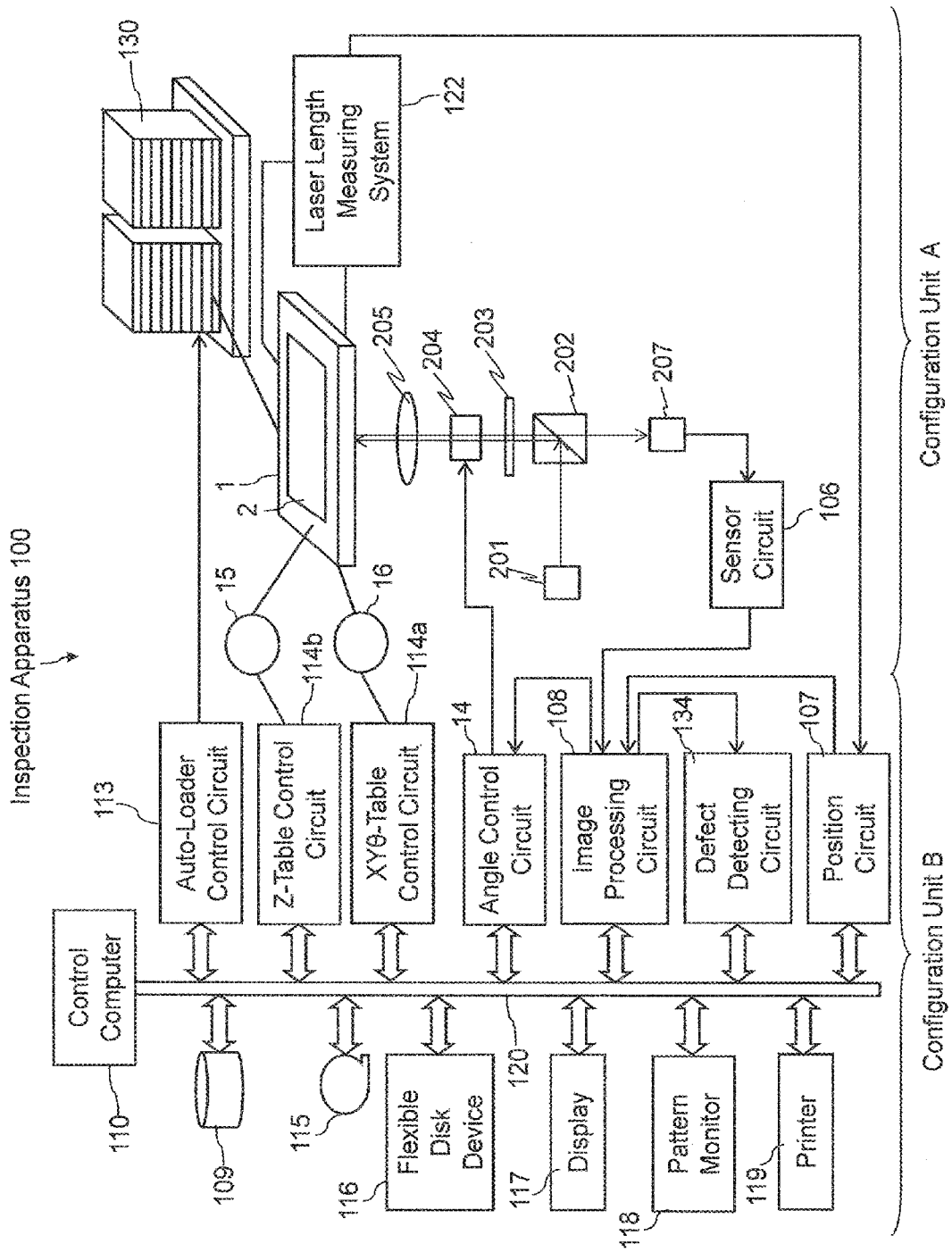
FIG. 9 is a configuration diagram of the inspection apparatus according to the first embodiment.

FIG. 9 is a configuration diagram of the inspection apparatus 100 according to the present embodiment. Each step of FIG. 8 is performed using the inspection apparatus 100 shown in FIG. 9. Firstly, the inspection apparatus 100 will be described.

The inspection apparatus 100 includes a configuration unit A that constitutes an optical image acquisition circuit and a configuration unit B that performs processing necessary for an inspection using an optical image acquired by the configuration unit A.

In the configuration unit A, the template 2 is positioned on the table 1. Therefore, the table 1 includes the XYθ-table (not illustrated in FIG. 9) that is movable in the horizontal direction and the θ-direction and the Z-table that is movable in the vertical direction.

In the configuration unit B, the control computer 110 for controlling the inspection apparatus 100 is connected to a position circuit 107, a image processing circuit 108, an angle control circuit 14, defect detecting circuit 134, an auto-loader control circuit 113, an XYθ-table control circuit 114a, a Z-table control circuit 114b, a magnetic disk device 109 as one example of storage, a magnetic tape device 115, a flexible disk device 116, a display 117, a pattern monitor 118, and a printer 119 through a bus 120 that constitutes a data transmission line.

In the configuration unit A, the table 1 is driven by an XYθ-driving mechanism 16 that is controlled by an XYθ-table control circuit 114a in the horizontal direction and θ-direction. The table 1 is driven by the Z-driving mechanism 15 that is controlled by a Z-table control circuit 114b in the perpendicular. A moving position of the table 1 is measured by the laser length measuring system 122, and transmitted to the position circuit 107. The template 2 is automatically conveyed to the table 1 by the auto-loader 130 driven by the auto-loader control circuit 113. After the inspection is finished, the template 2 is automatically discharged by the auto-loader 130.

The optical image of the pattern of the template 2, that is the inspection object, is acquired in the configuration unit A. Specifically, it will be described as follows.

The light emitted from a light source 201 is reflected by a polarization beam splitter 202, and incident on the Faraday rotator 204 through a half-wavelength plate 203. The image of the light transmitted through the Faraday rotator 204 is formed in the inspection area of the template 2 by an objective lens 205. Then, the light reflected by the template 2 is transmitted through the objective lens 205, transmitted through the Faraday rotator 204, the half-wavelength plate 203, and the polarization beam splitter 202, and incident on a sensor 207. The sensor 207 captures the optical image of the pattern of the template 2.

The sensor 207 stores a weak expanded optical image of the template 2, and converts the optical image to an electrical signal of the image and then outputs the electrical signal. The TDI sensor is an area sensor the exposure area of which can be divided into N-sections. The N-sections are provided along the integration direction for integrating a charge. When the optical image of the template 2 is acquired, the direction of the movement of the table 1 is matched to the integration direction of the TDI sensor. Next, when the TDI sensor is scanning the template 2, a charge is transferred in every step along the integration direction and the charges corresponding to several integrated sections are stored and output. Thereby, even if a charge of one section is weak, the output can be obtained by the accumulation of several sections, that is, the addition of sections, wherein the output corresponds to several tens of the light quantity of the light quantity in the case where the addition is not performed, by the same scan time as the time in the case where the addition is not performed.

According to the inspection method of the present embodiment, firstly, the template 2 is positioned on the table 1, and then plate alignment is performed (S1). By the plate alignment, the XY-coordinate axes of the imprint surface of the template 2 are aligned parallel and perpendicular to a traveling axis of the table 1 in the inspection apparatus 100. Thereby, a rotation error or an extension and contraction error of the pattern disposed in the template 2 is normalized with respect to the optical system of the inspection apparatus 100. Specifically, the plate alignment is performed as follows.

When the template 2 is placed at the predetermined position on the table 1, a rotation angle θ from the predetermined position of the template 2 or the whole extension or contraction of the pattern due to a temperature fluctuation can be automatically calculated by an amendment calculation in the inspection apparatus 100. At this time, the rotation angle and extension and contraction of the pattern are calculated using the alignment mark.

Firstly, the X-axis and Y-axis of the two alignment marks that are provided in the template 2 to establish a horizontal or vertical position relationship are adjusted so as to be parallel or perpendicular to the traveling axis of the table 1. For example, in FIG. 5, when the X-axis of the alignment mark provided in the alignment mark area AM102 coincides with the X-coordinate axis of the alignment mark provided in the alignment mark area AM103, the Y-coordinate axis of the pattern of the template 2 is matched to the Y-coordinate axis of the table 1. Further, when the Y-coordinate axis of the alignment mark provided in the alignment mark area AM101 coincides with the Y-coordinate axis of the alignment mark provided in the alignment mark area AM108, the X-coordinate axis of the pattern of the template 2 is matched to the X-coordinate axis of the table 1.

Further, the template 2 is adjusted so as to be located at the predetermined position by rotating a θ-axis of the table 1 based on the alignment mark, and then a distance between the two alignment marks is measured. An extension and contraction ratio of the template 2 is calculated by comparing the measured distance to a theoretical distance between the alignment marks, which are previously provided to the inspection apparatus 100. Accuracy of an inspection result can be enhanced by reflecting the obtained value on the correction calculation of the position and dimension of the pattern to be measured in the inspection process.

Next, the amplitude of the light quantity of the sensor 207 for acquiring the optical image of the template 2 is optimized (S2). Specifically, the gain of the amplifier of each pixel is adjusted so that the amplitude of the signal of each pixel of the sensor 207 becomes equal. The offset and amplitude of the brightness are adjusted so that the strength of the signal for the defect detection can be set to a maximum level for ease of the inspection by utilizing the maximum dynamic range of white and black amplitude of the optical image of the template 2.

Next, the focus offset is adjusted by using the programmed defect provided in the focus offset adjusting pattern area of the template 2 (S3).

Specifically, the optical image of the programmed defect is acquired while the focal distance between the imprint surface of the template 2 and the objective lens 205 is changed, and the optimum focal distance for detecting the programmed defect, that is, the focal distance for setting the signal-to-noise (S/N) ratio of the optical signal to the maximum level, is obtained. The focal distance is displaced from the focal position by the focus offset. The focal distance can be adjusted by changing the height of the table 1.

As the programmed defect is disposed in the second pattern, the optical image of the programmed defect is specifically the optical image of the programmed defect disposed in the second pattern. The second pattern is a repetitive pattern like the first pattern. Therefore, it is necessary that the direction of the movement of the table 1, during the acquisition of the optical image of the programmed defect, is parallel to the repetitive direction of the first and second patterns, or perpendicular to the repetitive direction of the first and second patterns based on the direction of the third pattern.

As one example, a plurality of chip patterns consisting of the same construction are provided in the whole of the template 2 or a part of the template 2. Specifically, the repetitive pattern for the same integration circuit to be imprinted to the wafer is provided. The repeated integration circuit has a rectangular shape having the same dimension, and is referred to as a dye once the integration circuit is separated from each other. In one dye an integration circuit as one unit is ordinarily formed. When the repetitive pattern is inspected by the die-to-die comparison method, optical images of the same patterns formed in different chips are compared with each other.

For example, when the optical image of the n-th chip is the inspection target, the optical image of the (N−1)-th chip is a reference image to be compared. In this case, if the repetitive pattern is a pattern which cannot be resolved by the wavelength of the light source of the inspection apparatus, the optical images having a uniform gray gradation value in almost all of the inspection areas are compared. However, in the optical image including a defect of the pattern, a defect location is observed as a white spot or a black spot depending on the types or shapes of the defect.

For example, in the case where the optical image of the repetitive pattern is acquired by irradiating the template 2 with light, causing the reflected light to be incident to the sensor 207, if the neighboring pattern is bridged as a result of connecting with each other, the light reflected from that location is more intense than light reflected at other locations as the bridged location has a larger area to reflect light, and as a result the defect is observed as a white spot. On the other hand, if the pattern has the broken pattern defect, the light reflected from that location is less intense than light reflected at other locations as in the broken defect location the pattern lacks the area for reflecting light, that is, the area is smaller, and as a result the defect is observed as a black spot. In these cases, when the focus offset is changed, the brightness or the shape of the black spot at the defect location is changed and/or the signal amplitude of the maximum value and minimum value of the defect signal is changed.

In the focus offset adjusting step, the optimum focus offset for detecting a defect is searched. Specifically, as mentioned above, while the focus offset is changed, that is, the focal distance between the imprint surface of the template 2, and the objective lens 205 is changed, the optical image of the programmed defect disposed in the focus offset adjusting pattern area is acquired, and a focal distance for setting the signal-to-noise ratio of the programmed defect to the maximum level, is searched. For example, the method for calculating the brightness signal level of a defect to the signal level of the gray gradation value by a predetermined algorithm is adapted.

Causes that may influence the focus offset include the dimension of the pattern to be imprinted to the wafer, formed in the template 2; a depth for digging in the imprint surface; and the condition of a coating of the surface of the template 2, etc., in addition to the types, shape, and size of a defect. Further, in the inspection apparatus 100, there is a possibility that the optimum position of the focus offset for a defect such as a broken pattern defect differs to the optimum position of the focus offset for a defect such as a bridge pattern defect depending on the illumination optical system for illuminating the template 2 with the light from the light source 201 and/or the imaging optical system for focusing the transmitted or reflected light from the template 2 to be incident to the sensor 207. In this case, it is preferable that the inspection is performed twice using different focus offset values, for example, in the first inspection, the inspection is performed using the optimum focus offset value for a broken pattern defect, and then in the second inspection, the inspection is performed using another optimum focus offset value for a bridge pattern defect.

As a result of searching, when an optimum focus offset value is determined, the focal distance between the imprint surface of the template 2 and the objective lens 205 is adjusted to the optimum focus offset value.

After the focus offset value is adjusted, each step S4 to S6 illustrated in FIG. 8 is performed, that is, a rotation angle of a polarization plane of light by the faraday rotator 204 is determined (S4), next, the optical image for the inspection is acquired (S5), and then the existence of a defect is determined based on the optical image acquired in S5 (S6).

The Faraday rotator 204 rotates the light polarization plane by a Faraday effect. The Faraday effect is a phenomenon in which, when a magnetic field is applied to the same direction as the light traveling direction while linearly polarized light is incident on an optical material, phase speeds of two components (right-handed circularly polarized light and left-handed circularly polarized light) of the linearly polarized light deviate from each other, and therefore the polarization plane of the light (linearly polarized light) output from the optical material rotates by the phase difference at an exit location.

Figure 10:
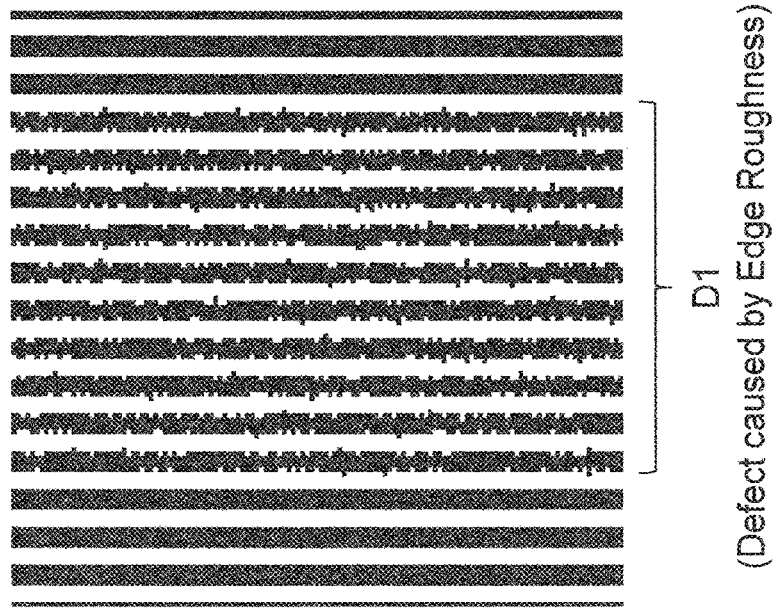
FIG. 10 is a view illustrating a defect caused by the edge roughness.

Among the pattern defects, the pattern bridge defect in which the lines are short-circuited with each other and the broken pattern defect in which the line is disconnected have a serious influence on the performance of the template. On the other hand, edge roughness observed in the area D1 of FIG. 10 has a limited influence on the template compared with the pattern bridge defect or the broken pattern defect. Therefore, the edge roughness is not necessarily detected in the inspection.

However, in the case that the pattern bridge defect, the broken pattern defect, and the edge roughness having the size that is less than the optical resolution limit are mixed in the same pattern, more particularly the same repetitive pattern having a period that is less than the optical resolution limit of the optical system in the inspection apparatus, in observation with the optical system, the brightness and darkness caused by the pattern bridge defect or the broken pattern defect is not distinguished from the brightness and darkness caused by the edge roughness. This is because, in the optical image of the pattern, all of the defects, that is, the pattern bridge defect, the broken pattern defect, and the edge roughness become blurred by the same amount, that is, these defects are expanded to the same dimension, namely, to about the optical resolution limit of size.

Figure 11:
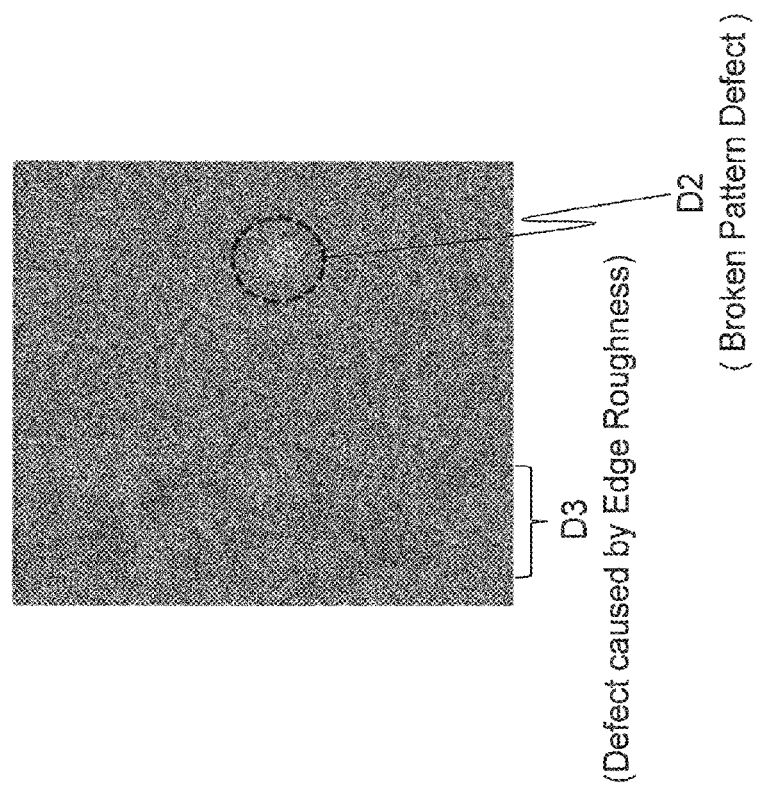
FIG. 11 is a view illustrating a defect caused by the edge roughness, and a broken pattern defect.

FIG. 11 schematically illustrates the line-and-space pattern provided in the template. In FIG. 11, it is assumed that the dimension of the pattern is smaller than the resolution limit of the optical system. In the area D2, the line pattern is partially lacking thus generating the broken pattern defect. In the area D3, the edge roughness of the line pattern becomes prominent.

A broken pattern defect and a defect caused by the edge roughness can be clearly distinguished because the difference is obvious on the template as shown in FIG. 11. However, it is hard to distinguish between these defects when these defects are observed via the optical system of the inspection apparatus, that is, whether the defect is a broken pattern defect or a defect caused by the edge roughness. This is because the optical system behaves as a spatial frequency filter defined by a wavelength $\lambda$ of the light emitted from the light source and a numerical aperture NA.

Figure 12:
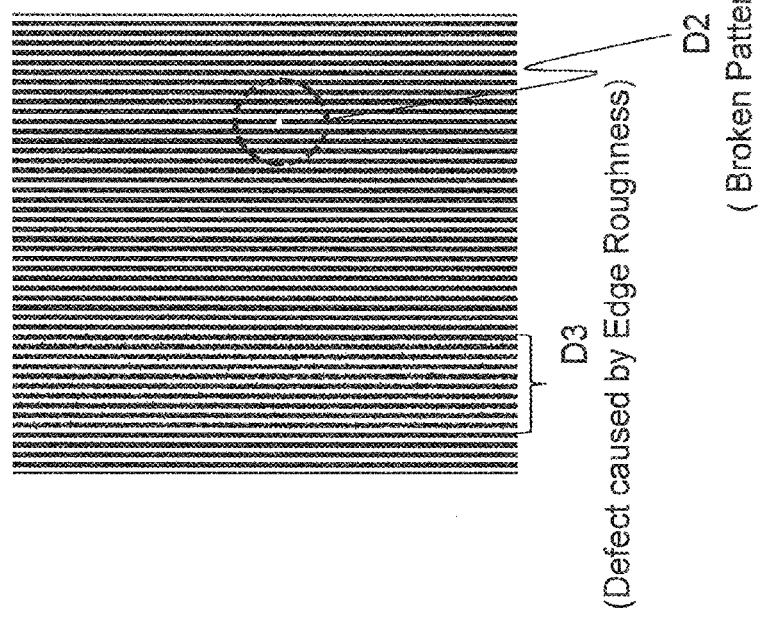
FIG. 12 is a view illustrating the pattern in FIG. 11 to which the spatial frequency filter is applied.

FIG. 12 illustrates a state in which the pattern in FIG. 11 is subjected to the spatial frequency filter. As can be seen from FIG. 12, the defect in the area D2 and the defect in the area D3 are expanded to the similar dimension, and the shapes of the defects are not distinguishable from each other. Thus, in principle, the broken pattern defect that is less than the optical resolution limit and the edge roughness that is less than the optical resolution limit are not distinguished from each other by the optical system. The same holds true for the pattern bridge defect and the defect caused by the edge roughness.

The large defect such as the pattern bridge defect and the broken pattern defect has the large influence on the polarization state of the illumination light compared with the small defect such as the defect caused by the edge roughness. Therefore, the influence of the bridge pattern defect and the broken pattern defect on the polarization state of the irradiation state is larger than the defect caused by the edge roughness. For example, in the pattern bridge defect, a vertical direction and a horizontal direction differ from each other in sensitivity for an electric field component of the illumination light. Specifically, this will described as follows.

For the sake of easy understanding, it is considered that the linearly-polarized light is perpendicularly incident to the template. In the case that the linearly-polarized light has the polarization direction of 45 degrees with respect to a direction along an edge of the line-and-space pattern, while a vertical component and a horizontal component of the electric field of the incident light are equal to each other, a difference between the horizontal component and the vertical component of the electric field of the reflected light emerges due to the pattern bridge defect, that is, the horizontal component becomes larger than the vertical component. As a result, the polarization direction of the light reflected from the pattern bridge defect becomes inclined in the direction intersecting the direction of the edge of a line-and-space pattern. Also, in the same example, in the case of the broken pattern defect, the polarization direction becomes inclined in the direction along the edge of a line-and-space pattern.

On the other hand, for the defect caused by the edge roughness, the adjacent lines are not connected to each other, and the lines are not disconnected. Because a size of irregularities in the edge roughness is finer than the pattern bridge defect and the broken pattern defect, sensitivity between the vertical and horizontal directions of the electric field component of the illumination light is not so large. Therefore, in the case that the linearly-polarized light is perpendicularly incident to the template, the polarization direction of the light scattered by the edge roughness becomes a value close to 45 degrees of the polarization direction of the incident light when the linearly-polarized light has the polarization direction of 45 degrees with respect to the direction along the edge of the line-and-space pattern. However, because the polarization direction is influenced by a base pattern having the periodic repetition, the polarization direction does not completely become 45 degrees, but the polarization direction has the value slightly deviated from 45 degrees.

As mentioned above, when the light having the polarization plane of 45 degrees is illuminated relative to the direction of the repetitive pattern formed on the template 2, a difference in sensitivity between a large defect such as a bridge pattern defect and a broken pattern defect, and a small defect such as a defect caused by the edge roughness of the electronic field component of the light, is caused. On the other hand, when the polarization plane of the light is 0 degrees or 90 degrees relative to the direction of the repetitive patterned formed on the template 2, the sensitivity of the light between the large defect and the small defect is the same, therefore, the type of defect cannot be distinguished. That is, it is not necessary that the polarization plane of the light is exactly 45 degrees relative to the direction of the repetitive pattern, however it is important that the polarization plane of the light is not 0 degrees or 90 degrees. In other words, it is preferable that the polarization plane of the light to be incident to the template 2 is at any angle except an angle in the range of −5 degrees and 5 degrees, and except an angle in the range of 85 degrees and 95 degrees.

The pattern bridge defect or the broken pattern defect differs from the defect caused by the edge roughness in the influence on the polarization state of the illumination light. Accordingly, even if the pattern is finer than the optical resolution limit of the optical system, the defect can be classified by taking advantage of the difference. Specifically, by controlling the polarization state of the illumination light and the condition for the polarization control element, that is, Faraday rotator 204 of the present embodiment, in the optical system that images the light reflected from the template, the bright and dark unevenness caused by the edge roughness can be removed with the polarization control element to extract only the change in amplitude of the pattern bridge defect or broken pattern defect.

In the present embodiment, the rotation angle of the faraday rotator is determined in S4 shown in FIG. 8. In the step of S4, the rotation angle of the polarization plane of the light rotated by the Faraday rotator, corresponding to the minimum standard deviation of the gradation value is determined by obtaining the gradation value of each pixel regarding the optical image of the pattern of the template 2, acquired in the previous step. Or, depending on the situation, the step of S4 can be a step for obtaining a rotation angle, for minimizing a value, which is obtained by dividing the standard deviation of the gradation values, of a plurality of optical images obtained by changing the rotation angle of the polarization plane of the light rotated by the Faraday rotator, by a square root of an average gradation value obtained from the gradation value. In any cases, it is preferable that the optical image is an optical image of the programmed defect disposed in the template 2.

In S4, in the inspection apparatus 100, the rotation angle (Faraday rotation angle θ) of the polarization plane of light rotated by the Faraday rotator 204, is determined to minimize the quantity of light, emitted from the light source 201 for illuminating the template 2, which is scattered by the edge roughness and incident to the sensor 207. By disposing a defect simulating the edge roughness in the focus offset adjusting pattern area, the condition for removing the bright and dark unevenness caused by the light scattered by the edge roughness, that is, the Faraday rotation angle θ for minimizing the light quantity scattered by the edge roughness to be incident to the sensor 207, can be obtained using the optical image. The optical image which is used in the step for adjusting the focus offset (S3), can be the above-mentioned optical image.

In the inspection apparatus 100 as shown, the rotation angle (Faraday rotation angle θ) of the polarization plate of the light is changed by the Faraday rotator 204 such that the light scattered by the edge roughness of the template 2 is prevented from being incident to the sensor 207. The light scattered by the pattern bridge defect or broken pattern defect is separated from the light scattered by the edge roughness, and is incident to the sensor 207 through the half-wavelength plate 203 and the polarization beam splitter 202. Therefore, in the optical image captured with the sensor 207, the pattern bridge defect and the broken pattern defect are easily inspected, because the pattern bridge defect and the broken pattern defect are left while the bright and dark unevenness caused by the edge roughness is removed. That is, the optical image acquired with the sensor 207 can be used to inspect the pattern finer than the optical resolution limit of the optical system.

Figure 13:
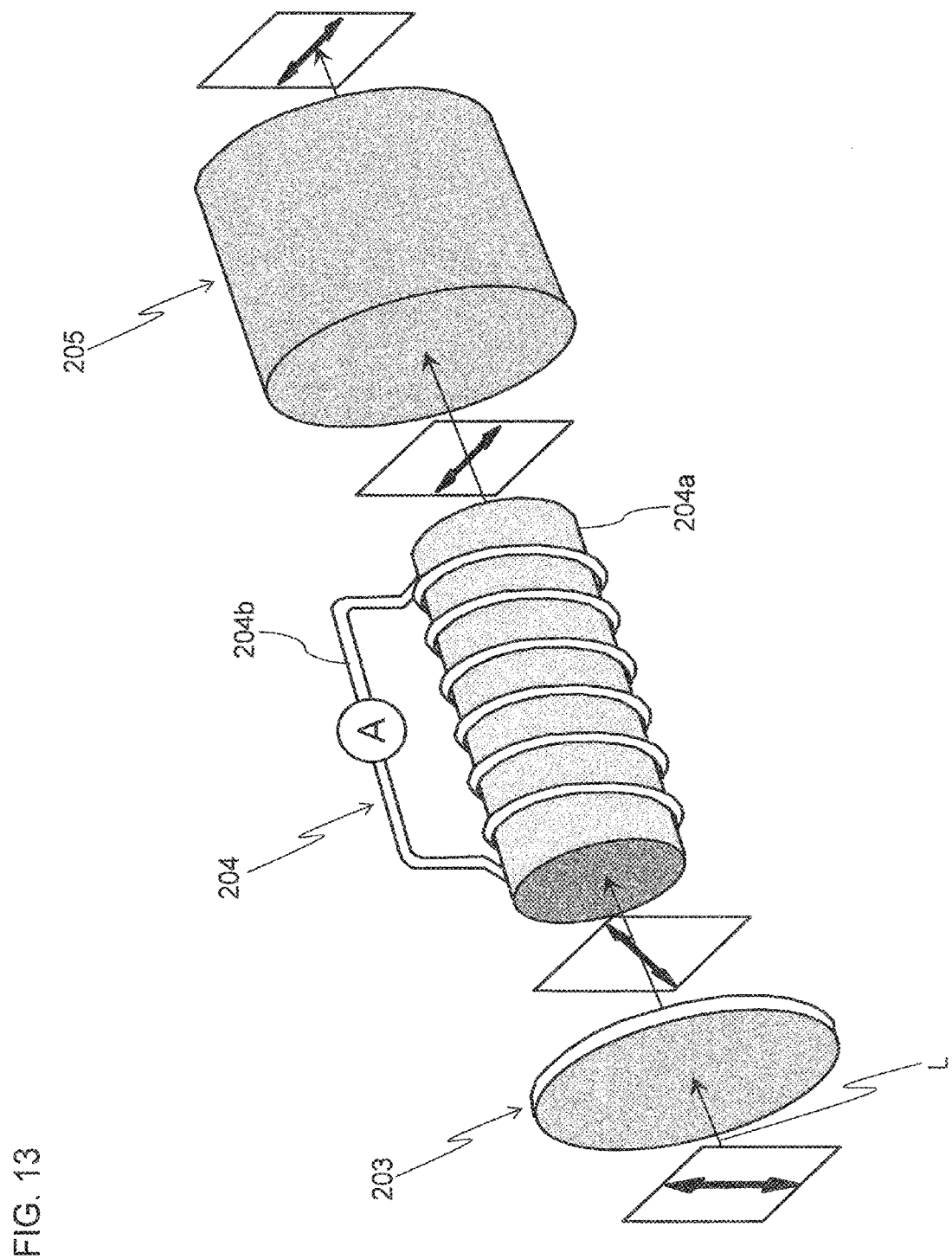
FIG. 13 is a view for explaining a state in which a polarization plane of light is rotated by the optical system in the inspection apparatus.
Figure 14:
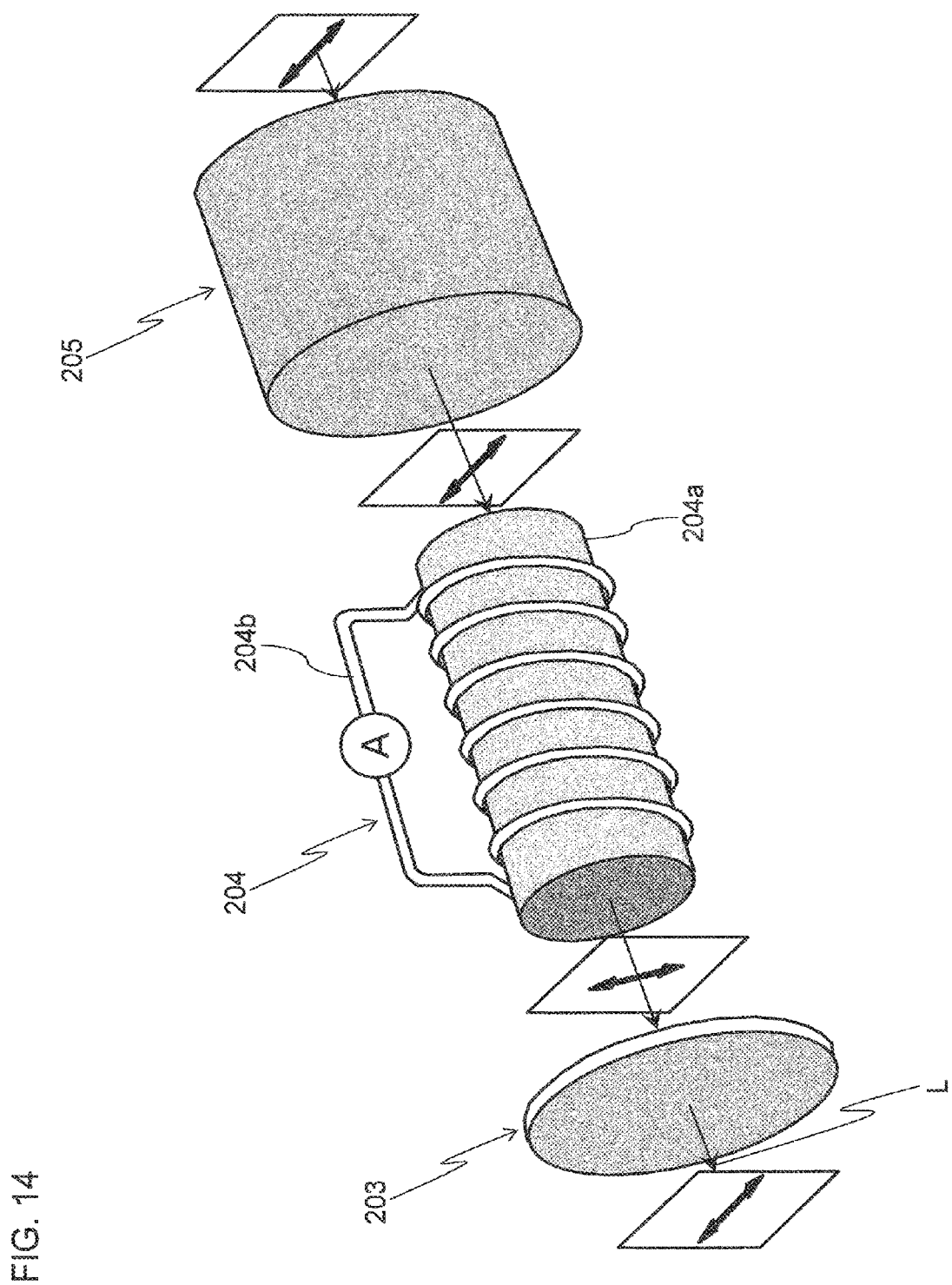
FIG. 14 is a view for explaining a state in which a polarization plane of light is rotated by the optical system in the inspection apparatus.

FIGS. 13 and 14 are views illustrating the rotation of the polarization plane of light by the optical system of the inspection apparatus 100.

As shown in FIGS. 13 and 14, the Faraday rotator 204 includes an optical material 204a that transmits light, and a coil 204b is wound around the optical material 204a. The optical material 204a is a material having a high transmittance to the light emitted from the light source 201. For example, in the case that the light source 201 emits the DUV light, a magneto-optical crystal having a high transmittance with respect to DUV light, such as $SiO_2$, $CaF_2$ or $MgF_2$ is used as the optical material 204a. The coil 204b is wound such that passage of a current applies a magnetic field to the optical material 204a in a direction parallel to a traveling direction of the light.

In the Faraday rotator 204, the intensity of the magnetic field applied to the optical material 204a is changed when the current passing through the coil 204b is changed. Accordingly, the rotation angle (Faraday rotation angle θ) of the polarization plane of light transmitted through the Faraday rotator 204 can be changed by controlling the intensity of the magnetic field.

The Faraday rotation angle θ is expressed by the following formula (3). Where H is the intensity of the magnetic field, l is a length of a material transmitting the polarized light, and V is a Verdet constant that depends on a type of the material, the wavelength of the polarized light, and temperature.

$$\theta = VHl \tag{3}$$

The above-mentioned materials $SiO_2$, $CaF_2$, and $MgF_2$ as the optical material 204a, do not have spontaneous magnetization. Therefore, it is necessary to apply the large magnetic field to these optical materials in order to obtain the desired Faraday rotation angle θ.

The Faraday rotation angle θ that properly separates the light scattered by the pattern bridge defect or the broken pattern defect from the light scattered by the edge roughness depends on the pattern structure. For this reason, in the inspection apparatus 100, the Faraday rotation angle θ is changed according to the pattern of the template 2. Specifically, an angle control circuit 14 changes the current passed through the coil of the Faraday rotator 204, and thereby the intensity of the magnetic field applied to the optical material 204a is changed such that the Faraday rotation angle θ is obtained according to the type of the pattern.

In the case that the permanent magnet is used in the Faraday rotator 204, it is preferable that multiple permanent magnets having different intensities of the magnetic field are provided. Then, the permanent magnet is selected, so that the Faraday rotation angle θ can be obtained depending on the type of the pattern, to apply the magnetic field necessary for the optical material.

The Faraday rotation angle θ is also changed by changing a thickness of the optical material. Accordingly, multiple optical materials having different thicknesses are prepared, and the optical material that can achieve the Faraday rotation angle θ corresponding to the type of the pattern may be selected among the multiple optical materials. In this case, the intensity of the magnetic field applied to the optical material can be made uniform irrespective of the optical material.

As mentioned above, the polarization plane of the light to be incident to the template 2 is preferably set to any angle except an angle within a range of an angle equal to or larger than −5 degrees and an angle equal to or smaller than 5 degrees, and a range of an angle equal to or larger than 85 degrees and an angle equal to or smaller than 95 degrees. Further, in the present embodiment, preferably the light is transmitted through the Faraday rotator 204 twice, that is, back and forth, to rotate the light polarization plane by 90 degrees. That is, preferably the magnetic field is applied to the optical material such that the light is rotated by 90 degrees while transmitted back and forth.

As illustrated in FIG. 13, linearly polarized light L is transmitted through the half-wavelength plate 203 to rotate the polarization plane of the linearly polarized light L by 45 degrees. Then, the linearly polarized light L is transmitted through the Faraday rotator 204 to further rotate the polarization plane of the linearly polarized light L by 45 degrees. Then, the image of the linearly polarized light L is formed on the template (not illustrated in FIG. 13) through the objective lens 205.

Referring to FIG. 14, the linearly polarized light L reflected by the template (not illustrated in FIG. 14) is transmitted through the objective lens 205, and incident on the Faraday rotator 204. Then, the linearly polarized light L is transmitted through the Faraday rotator 204 to rotate the polarization plane of the linearly polarized light L by 45 degrees. Then, the linearly polarized light L is transmitted through the half-wavelength plate 203 to rotate the polarization plane of the linearly polarized light L by −45 degrees.

Thus, the linearly polarized light L is transmitted through the Faraday rotator 204 twice to rotate the polarization direction of the linearly polarized light L by 90 degrees. Therefore, in FIG. 9, the light emitted from the light source 201 is reflected by the polarization beam splitter 202, and oriented toward the template 2. Because the polarization plane of the light reflected by the template 2 is rotated by 90 degrees, the light is transmitted through the polarization beam splitter 202, and the light is oriented toward the sensor 207, not the light source 201. When the light is incident on the sensor 207, the sensor 207 captures the optical image of the template 2.

Next, a method for determining the rotation angle of the Faraday rotator 204 (S4) will be described referring to FIG. 8. Thereby, the condition for removing light-dark unevenness caused by the edge roughness can be obtained.

Generally, there is a large amount of edge roughness existing in the whole surface of the template of the inspection target while very few number of pattern bridge defects or broken pattern defects exist in the template. For example, when the optical image having the area of 100 μm×100 μm is acquired, there is a small possibility that the pattern bridge defect or the broken pattern defect is included in the area, and there are very few defects existing in the area even if the pattern bridge defect or the broken pattern defect is included in the area. That is, almost all the optical images in the area are caused by the edge roughness. Accordingly, the condition that removes the defect caused by the edge roughness is obtained from one optical image having the dimension of approximately 100 μm×approximately 100 μm.

As mentioned above, the change in gradation value caused by the edge roughness in the optical image can be removed by controlling the polarization direction of the light incident to the sensor 207. Specifically, the quantity of light that is incident to the sensor 207, while being scattered by the edge roughness, is changed by controlling the Faraday rotation angle θ using the Faraday rotator 204, which allows the bright and dark amplitude to be changed in the optical image.

The bright and dark amplitude in the optical image is expressed by a standard deviation of the gradation value in each pixel. For example, assuming that the optical system has a pixel resolution of 50 nm in the inspection apparatus, the optical image having the area of 100 μm×100 μm is expressed by 4 million pixels. That is, a specimen of 4 million gradation values is obtained from the one optical image.

For a dark-field illumination system, the standard deviation is obtained with respect to the specimen, the obtained standard deviation is defined as a degree of the scattering light caused by the edge roughness, and the polarization state on the imaging optical system side, namely, the Faraday rotation angle θ is adjusted such that the standard deviation becomes the minimum. Therefore, the quantity of scattering light incident to the sensor 207 due to the edge roughness can be minimized.

For the optical image in a bright-field optical system, a degree of the brightness and darkness caused by the edge roughness is influenced by zero-order light. The reason is as follows. Because the periodic pattern finer than the optical resolution limit exists in the inspection target, the polarization state of the zero-order light changes due to a phase-difference effect caused by structural birefringence. Therefore, the light quantity that becomes a base also changes when the Faraday rotation angle θ is changed in order to remove the reflected light caused by the edge roughness. Because the bright-field image is a product of an electric field amplitude of the scattering light from the pattern bridge defect, the broken pattern defect, or the edge roughness and an electric field amplitude of the zero-order light, the degree of the brightness and darkness caused by the edge roughness is influenced by an intensity of the zero-order light.

In order to remove the influence of the scattering light due to the edge roughness to improve the detection sensitivity for the pattern bridge defect or broken pattern defect, it is necessary to find, not the condition in which a function (specifically, a function expressing the electric field amplitude of the zero-order light) caused by the zero-order light becomes the minimum, but the condition that a function (specifically, a function expressing the electric field amplitude of the scattering light caused by the edge roughness) caused by the edge roughness becomes the minimum. The reason the function caused by the zero-order light becomes the minimum is that the function caused by the zero-order light is the condition that the base light quantity simply becomes the minimum but the influence of the edge roughness is not completely removed.

The function caused by the edge roughness becoming the minimum is obtained by a calculation using a standard deviation σ of the gradation value of the optical image and an average gradation value A. The standard deviation σ includes various noise factors, and particularly the standard deviation σ is largely influenced by the brightness and darkness caused by the edge roughness. The average gradation value A of the optical image is the base light quantity, namely, the intensity of the zero-order light. The electric field amplitude of the scattering light due to the edge roughness is proportional to a value in which the standard deviation σ of the optical image is divided by a square root of the average gradation value A. In order to find the condition that minimizes the bright and dark amplitude caused by the edge roughness, the optical image is acquired while the Faraday rotation angle θ is changed, and the value (σ/√A) in which the standard deviation of the gradation value in the obtained optical image is divided by the square root of the average gradation value is calculated. The Faraday rotation angle θ is obtained when the value (σ/√A) becomes the minimum.

As mentioned above, for the large defect such as the pattern bridge defect and the broken pattern defect, the vertical direction and the horizontal direction differ from each other in the sensitivity to the electric field component of the illumination light. Accordingly, when the electric field amplitude of the scattering light caused by the large defect becomes the minimum, the Faraday rotation angle θ differs from that of the scattering light caused by the edge roughness. That is, even if the Faraday rotation angle θ is applied when the electric field amplitude of the scattering light caused by the edge roughness becomes the minimum, the electric field amplitude of the scattering light caused by the pattern bridge defect or the broken pattern defect does not become the minimum. Therefore, the pattern bridge defect and the broken pattern defect can be detected without being buried in the amplitude of the brightness and darkness caused by the edge roughness.

As described above the Faraday rotation angle θ that properly separates the light scattered by the pattern bridge defect or the broken pattern defect from the light scattered by the edge roughness depends on the pattern structure. The detail is described as follows.

When the electric field amplitude of the scattering light caused by the edge roughness becomes the minimum, the Faraday rotation angle θ depends on a structure of the pattern formed in the inspection target. For example, Faraday rotation angle θ at which the electric field amplitude of scattering light caused by the edge roughness becomes the minimum also changes when a pitch of the pattern, a depth of the dugout portion, or a line-and-space ratio of the pattern changes. Accordingly, it is necessary that the Faraday rotation angle θ is obtained depending on the construction of the pattern of the inspection target. That is, in the case where the identical pattern to be inspected is disposed in the template, the Faraday rotation angle θ which is obtained in the preliminary inspection, can be used in the inspection process, however, in the case that a plurality of patterns each having a different structure are provided in the inspection target, it is necessary to change the Faraday rotation angle θ according to the pattern. Additionally, even in the identical design pattern, the depth or the line-and-space ratio is slightly changed by various error factors, and possibly the Faraday rotation angle θ that minimizes the electric field amplitude of the scattering light, varies in the template. In this case, it is necessary to follow the variation to change the Faraday rotation angle θ.

The rotation angle of the Faraday rotator 204 for removing light-dark unevenness caused by the edge roughness can be obtained by the inspection apparatus 100 as shown in FIG. 9.

Firstly, while the Faraday rotation angle θ is changed, the optical image of the programmed defect disposed in the focus offset adjusting pattern area of the template 2 is acquired by the sensor 207. Specifically, the intensity of the current passed through the coil of the Faraday rotator 204 is changed by the angle control circuit 14. Thereby, the intensity of the magnetic field applied to the optical material is changed so that the predetermined Faraday rotation angle θ is obtained. In this case, one optical image having the dimension of approximately 100 μm×approximately 100 μm may be obtained in each predetermined value of the Faraday rotation angle θ. The obtained data of the optical image is transmitted to the image processing circuit 108 through the sensor circuit 106.

The optical image is expressed by the gradation value of each pixel in the image processing circuit 108. Therefore, in the dark-field illumination system, the standard deviation is obtained with respect to one optical image, the obtained standard deviation is defined as the degree of the scattering light caused by the edge roughness, and the Faraday rotation angle θ is obtained such that the standard deviation becomes the minimum. On the other hand, in the bright-field illumination system, the optical image is acquired while the Faraday rotation angle θ is changing, and then calculates a value in which the standard deviation σ of the average gradation value in the acquired optical image is divided by the square root of the average gradation value A. The Faraday rotation angle θ is obtained when the value becomes the minimum. Using the Faraday rotation angle obtained as mentioned above, the light scattered by the edge roughness among the light from the template 2 is prevented from being incident to the sensor 207.

Information on the Faraday rotation angle θ obtained by the image processing circuit 108 is sent to the angle control circuit 14. The angle control circuit 14 controls the current passed through the coil of the Faraday rotator 204 according to the information from the image processing circuit 108. Therefore, the intensity of the magnetic field applied to the optical material of the Faraday rotator 204 can be changed to set the Faraday rotation angle θ to the value obtained by the image processing circuit 108.

After the rotation angle of the Faraday rotator is determined, as mentioned above, the optical image of the template 2 is acquired (S5), and then the existence of a defect is determined based on the optical image (S6).

Firstly, the intensity of the current passed through the coil of the Faraday rotator 204 is controlled by the angle controlling circuit 14, according to the information from the image processing circuit 108, so that the Faraday rotation angle θ becomes the value obtained in S4. In this state, the optical image of the pattern to be inspected, disposed in the imprint surface of the template 2, that is, the optical image of the first pattern (not shown) to be imprinted to the wafer, is acquired (S5).

The acquisition of the optical image in the step of S5 is specifically performed as follows.

In the inspection apparatus 100, the light emitted from the light source 201 is reflected by the polarization beam splitter 202, and then travels to the template 2. The light reflected by the template 2 can be transmitted through the polarization beam splitter 202 by rotating the polarization direction by 90 degrees. As a result, the light travels to the sensor 207 not the light source 201. Then, the optical image of the template 2 is acquired by causing the light to be incident to the sensor 207.

An area to be inspected in the template 2 is vertically divided into stripe-shaped multiple areas. Further, a plurality of units, each unit represented by "F", in which optical images are acquired (hereinafter, each unit is referred to as "frame"), are divided in a grid shape vertically set in each stripe. Each frame is preferably a square having each side equal to the width of the stripe, or a square wherein each side of the square is a width of the stripe divided into approximately four, that is, the perimeter of the square is equal to the width of the stripe.

Figure 15:
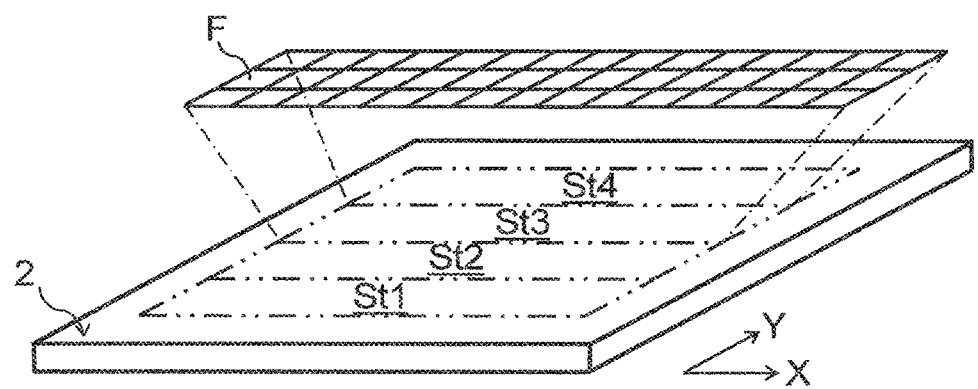
FIG. 15 is a view for explaining a relationship between an inspection area of a template, and a stripe and frame of the inspection area.

FIG. 15 is a view for explaining a relationship between an inspection area of a template, and a stripe and frame of the inspection area. In this example, the area to be inspected is hypothetically divided by four stripes ST1 to ST4. Furthermore, in each stripe ST1 to ST4, 45 frames are hypothetically set.

Each stripe ST1 to ST4 has a long shape extending along the X-direction and are arranged along the Y-direction. On the other hand, each frame includes a rectangular shape, for example, a length of one side is several tens of micrometers. In this case, in order to acquire the complete optical image, that is, to prevent the leakage of acquiring the optical image between two frames adjacent frames, the edge of one frame is positioned so that the edge is overlapped to the edge of another frame by a predetermined width. The predetermined width can be a width corresponding to 20 pixels of the TDI sensor, for example. The edges of the adjacent stripes are set so that the edges overlapped each other in the same manner as the frames.

Next, the optical image of the template 2 is acquired in each stripe. That is, in acquiring the optical image as shown in FIG. 15, the operation of the table 1 is controlled such that each stripe $St_1$, $St_2$, $St_3$, $St_4$, . . . is continuously scanned. Specifically, the optical image of the stripe $St_1$ is sequentially acquired along X-direction while the table 1 is moved in the −X-direction as shown in FIG. 15. The optical image is continuously input to the TDI sensor. The optical image of the stripe $St_2$ is acquired after the optical image of the stripe $St_1$ is acquired. In this case, after the table 1 moves in the −Y-direction in a stepwise manner, the optical image is acquired while the table 1 moves in the direction (X-direction) opposite to the direction (−X-direction) in which the optical image of the stripe $St_1$ is acquired, and the optical image of the stripe $St_2$ is continuously input to the TDI sensor. When the optical image of the stripe $St_3$ is acquired, after moving the table 1 in the −Y-direction in the stepwise manner, the table 1 moves in the direction opposite to the direction (X-direction) in which the optical image of the stripe $St_2$ is acquired, namely, the direction (−X-direction) in which the optical image of the stripe $St_1$ is acquired. The optical image of the stripe $St_4$ is acquired in the same manner as mentioned above.

In the step for acquiring the optical image in S5, the relationship between the direction of the movement of the table 1, and the repetitive direction of the first and second patterns, is maintained when the optical image is acquired in the focus offset adjusting step in S3. The repetitive direction of the first and second patterns can be easily obtained from the direction of the third pattern. Thereby, the direction of the first pattern, in the step for obtaining the optimum value of the focus offset, coincides with the direction of the first pattern, in the step for acquiring the optical image, in the inspection process to acquire the optical image at the optimum focus position.

The image of the pattern of the template 2 acquired by the sensor 207 is converted to the optical image data to be used in the inspection. This process will be specifically described as follows.

After the optical image of the pattern is incident to the sensor 207, the optical image is subjected to photoelectric conversion, and is further subjected to A/D (Analog to Digital) conversion by the sensor circuit 106, thus becoming optical image data. After that, the optical image data is transmitted to the image processing circuit 108.

The light-dark unevenness caused by the edge roughness is removed from the optical image, therefore the existence of a bridge pattern defect and/or a broken pattern defect are easily determined.

In the image processing circuit 108, the optical image data is expressed by the gradation value of each pixel. For example, one of values of a 0 gradation value to a 255 gradation value is provided to each pixel using a gray scale having 256-level gradation values. Further, the inspection area of the template 2 is divided to predetermined unit areas to obtain the average gradation value of each unit area. The predetermined unit area may be a square area having a size of 1 mm×1 mm, for example.

The information regarding the gradation value obtained in the image processing circuit 108 is transmitted to a defect detecting circuit 134. The defect detecting circuit 134 determines the existence of a defect of the pattern to be inspected in the template 2 (S6 shown in FIG. 8).

The defect detecting circuit 134 sets two threshold values above and below an average gradation value as the middle of the predetermined range. When the gradation value transmitted from the image processing circuit 108 is over the threshold value, the location corresponding to the gradation value is determined as a defect by the defect detecting circuit 134. The gradation values are predetermined before the inspection. Then, the defect information obtained in the defect detecting circuit 134 is stored in the magnetic disk device 109, for example.

The inspection apparatus 100 can also have a review function in addition to the inspection function. As used herein, the review means an operation in which an operator determines whether the detected defect will become a problem from a practical point of view.

For example, a coordinate and an optical image of a location determined to be the defect by the defect detecting circuit 134 are sent to a review tool (not illustrated). An operator reviews the optical image by comparison with a standard image that is a model image. The defect information determined by the review can be stored as a defect information list in the magnetic disk device 109. As an example, a reference image produced by design data of the inspection target pattern is used as the standard image.

As described above, in the first embodiment, the programmed defect is formed in the template, and the focus offset value is adjusted using the programmed defect, so that the inspection can be performed while the optimum focus offset value is always maintained. Therefore, reliability of the inspection result can be enhanced.

According to the present embodiment, a pattern including the shape that reflects the direction of the pattern to be inspected, and the dimension more than the resolution limit of the optical system of the inspection apparatus, is disposed in the template. Thereby, the direction of the pattern to be inspected when the optimum value of the focus offset value is obtained, can be easily obtained. Therefore, the optical image at the optimum focal position can be acquired by matching the direction of the pattern during the acquisition of the optical image to the direction of the pattern including the shape and dimension described above.

Further, in the first embodiment, the condition that the unevenness of the light and darkness scattered by the edge roughness is removed, namely, the Faraday rotation angle θ at which the amount of light, which is scattered by the edge roughness and incident on the sensor 207, is minimized is found using the programmed defect formed in the template. Therefore, the pattern finer than the resolution limit of the optical system can accurately be inspected. More particularly, the optical image, in which the unevenness of the light and darkness caused by the edge roughness is removed, is acquired to be able to inspect the pattern bridge defect and the broken pattern defect.

Second Embodiment

In the first embodiment, it is mentioned that the focus offset is adjusted before the direction of the pattern to be inspected is obtained by providing the second and third patterns in the focus offset adjusting pattern area. On the other hand, in the second embodiment, the alignment mark area (the alignment mark and surrounding areas) has the function for adjusting the focus offset. In the present embodiment, the kind of alignment which is the purpose of the alignment mark is not specifically limited. That is as some examples of alignment, the position alignment between a wafer and a template, the position alignment between a lower film and upper film during the formation of multiple-layer wiring, and plate alignment during the inspection process, are all possible.

The pattern to be inspected according to the present embodiment is a circuit pattern disposed in the imprint surface of the template. The circuit pattern consists of a repetitive pattern such as a line-and-space pattern, namely, a regular pattern that is periodically repeated is formed in the area to be inspected of the template. At least a part of the pattern is a pattern which is not resolved by the wavelength of the light emitted from the light source of the inspection apparatus, that is, a pattern (first pattern) finer than the resolution limit of the optical system of the inspection apparatus. A pattern formed in a memory mat portion of a semiconductor chip can be cited as an example of the first pattern.

It is preferable that the alignment mark area is disposed in the scribe line area so as not to disturb a layout of the circuit pattern. The scribe line area is an area between the pattern area to be inspected of the template and the outer periphery of the imprint surface, more specifically, as described using FIG. 4 in the first embodiment.

In the case that the alignment marks are used for the plate alignment in the inspection process, the X-coordinate of each alignment mark coincides with one of the X-coordinates of other alignment marks, and the Y-coordinate of each alignment mark coincides with one of the Y-coordinates of other alignment marks. However, because the outline of the imprint surface has a complex shape consisting of concave and convex portions, the scribe line area also has the complex shape. Accordingly, it may be difficult to provide the alignment area so that the alignment marks are positioned in the ideal location. Therefore, for example, a plurality of alignment mark areas are disposed in each scribe line area of the four corners (or surrounding the four corners) close to the outer periphery portion of the imprint surface, then, the X-coordinate of the template pattern is matched with the X-coordinate of the table in the inspection apparatus when the Y-coordinates of two alignment marks in the alignment mark areas are matched with each other. Then, the Y-coordinate of the template pattern is matched with the Y-coordinate of the table in the inspection apparatus when the X-coordinates of the other two alignment marks are matched with each other.

FIG. 16 is a schematic plan view illustrating an imprint surface Sf1 of the template. In FIG. 16, the area Sf3 indicated by dotted lines is another imprint surface that is imprinted to the neighboring imprint surface of the imprint surface Sf1.

Alignment mark areas AM1, AM2, AM5, AM6, AM9, AM10, AM12, and AM13 are provided in the imprint surface Sf1. On the other hand, alignment mark areas AM3, AM4, AM7, AM8, AM11, AM14, AM15, and AM16 are provided in the imprint surface Sf3.

Regarding the imprint surface Sf1, the X-coordinate of the template pattern is matched with the X-coordinate of the table in the inspection apparatus when the Y-coordinates of the alignment marks provided in the alignment mark areas AM1 and AM2, or when the Y-coordinates of the alignment marks provided in the alignment mark areas AM5 and AM6, are matched with each other. Further, the Y-coordinate of the template pattern is matched with the Y-coordinate of the table in the inspection apparatus when the X-coordinates of the alignment marks provided in the alignment mark areas AM9 and AM10, or when the X-coordinates of the alignment marks provided in the alignment mark areas AM12 and AM13, are matched with each other.

Regarding the imprint surface Sf3, the X-coordinate of the template pattern is matched with the X-coordinate of the table in the inspection apparatus when the Y-coordinates of the alignment marks provided in the alignment mark areas AM3 and AM4, or when the Y-coordinates of the alignment marks provided in the alignment mark areas AM7 and AM8, are matched with each other. The Y-coordinate of the template pattern is matched with the Y-coordinate of the table in the inspection apparatus when the X-coordinates of the alignment marks provided in the alignment mark areas AM11 and AM14, or when the X-coordinates of the alignment marks provided in the alignment mark areas AM15 and AM16 are matched with each other.

Figure 18:
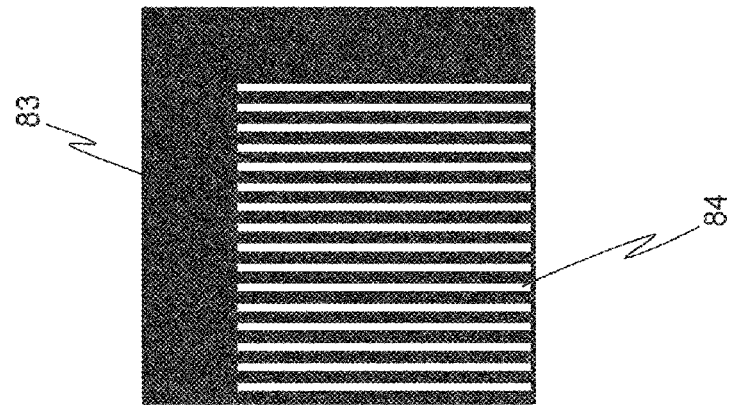
FIG. 18 is an expanded view of a part of FIG. 17.
Figure 17:
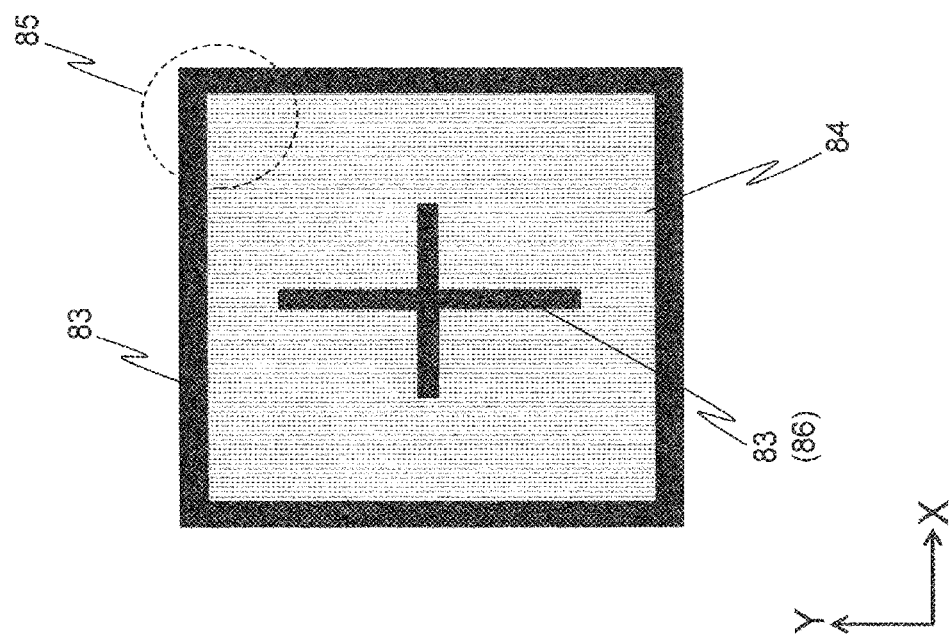
FIG. 17 is one example of the alignment mark area according to the second embodiment.

FIG. 17 is one example of the alignment mark area formed in the template. FIG. 18 is an expanded view of the area 85 illustrated in FIG. 17. The template is formed by digging the circuit pattern on the glass substrate, and does not have a shielding film as seen in a mask. Therefore, the alignment mark for the alignment in the template is formed by utilizing a difference of a contrast value between the existence or non-existence of the pattern. As illustrated in FIG. 17 and FIG. 18, the mark 86 having a cross shape which can be used as an alignment mark, is formed by utilizing a difference of a contrast value between an area (white area) in which the fine line-and-space pattern 84 is provided, and an area (black area) in which the matrix 83 of the template is seen because the line-and-space pattern 84 is not provided.

The line-and-space pattern 84 is the second pattern according to the present embodiment. The second pattern is a pattern following the first pattern (not shown) as the pattern to be inspected, and has the same shape and dimension as the first pattern. That is, the second pattern is also a finer pattern than the resolution limit of the optical system in the inspection apparatus.

The direction of the second pattern is the same as the first pattern. In the line-and-space pattern 84 as shown in FIG. 17, two edges of the longer side (edge) of the line pattern are extended in the Y-direction, and the line pattern is repeated in the X-direction. Therefore, the first pattern is also a line-and-space pattern in which two edges of the longer side (edge) of the line pattern are extended in the Y-direction, and the line pattern is repeated in the X-direction. When the first pattern is rotated by 90 degrees, two edges of the line pattern are extended in the X-direction, and the line pattern is repeated in the Y-direction. Further, when the second pattern is rotated by 90 degrees, two edges of the line pattern are extended in the X-direction, and the line pattern is repeated in the Y-direction, in the same manner as the first pattern.

The first pattern and second pattern are formed by digging a glass substrate to a depth of between 10 nm and 100 nm, for example.

As the first pattern and second pattern are finer than the resolution limit of the optical system of the inspection apparatus, these patterns cannot be resolved. According to the present embodiment, the alignment mark has a shape reflecting the direction of the first pattern and the second pattern so that the directions of the first pattern and the second pattern can be easily obtained. In FIG. 17, the mark 86 having the cross shape is the alignment mark. Two straight lines consisting of the mark 86 have the dimension larger than the resolution limit of the optical system of the inspection apparatus. Further, the length of one straight line is different to the other straight line, and the longer straight line is parallel to the Y-axis. That is, the direction of the longer straight line coincides with the direction of the extended edges of the first pattern and the second pattern. Therefore, the directions of the first pattern and second pattern can be easily obtained by the mark 86.

Figure 19:
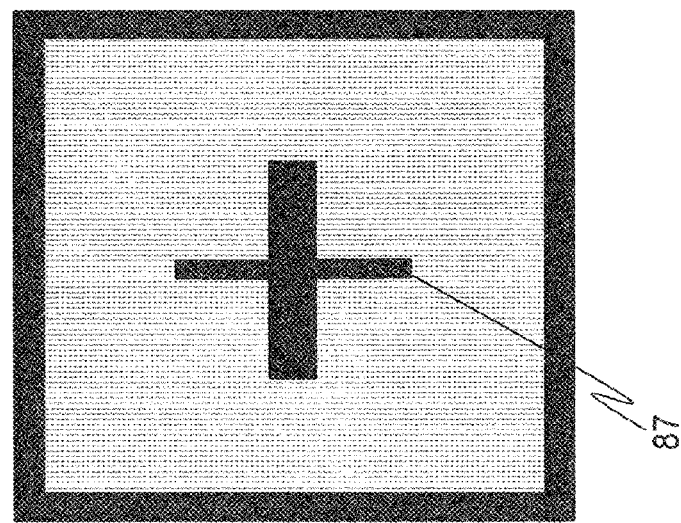
FIG. 19 is another example of the alignment mark area according to the second embodiment.

In the present embodiment, the shape of the alignment mark is not limited to the cross shape, and any shape may be used which can indicate the directivity of the first pattern and the second pattern. For example, the shape may be a shape of which two straight lines having different widths are combined to make a relationship between the width of the straight lines, and the directivity of the first pattern and the second pattern. In FIG. 19, the width of two straight lines consisting of the mark 87 having the cross shape are different. The thicker straight line is parallel to the X-axis. That is, the direction of the thicker straight line is perpendicular to the direction of the extended edges of the first pattern and the second pattern. On the other hand, regarding the thinner straight line, the direction of the thicker straight line is parallel to the direction of the extended edges of the first line and the second line. Therefore, the direction of the first pattern and the second pattern can also be easily obtained by the mark 87.

Figure 20:
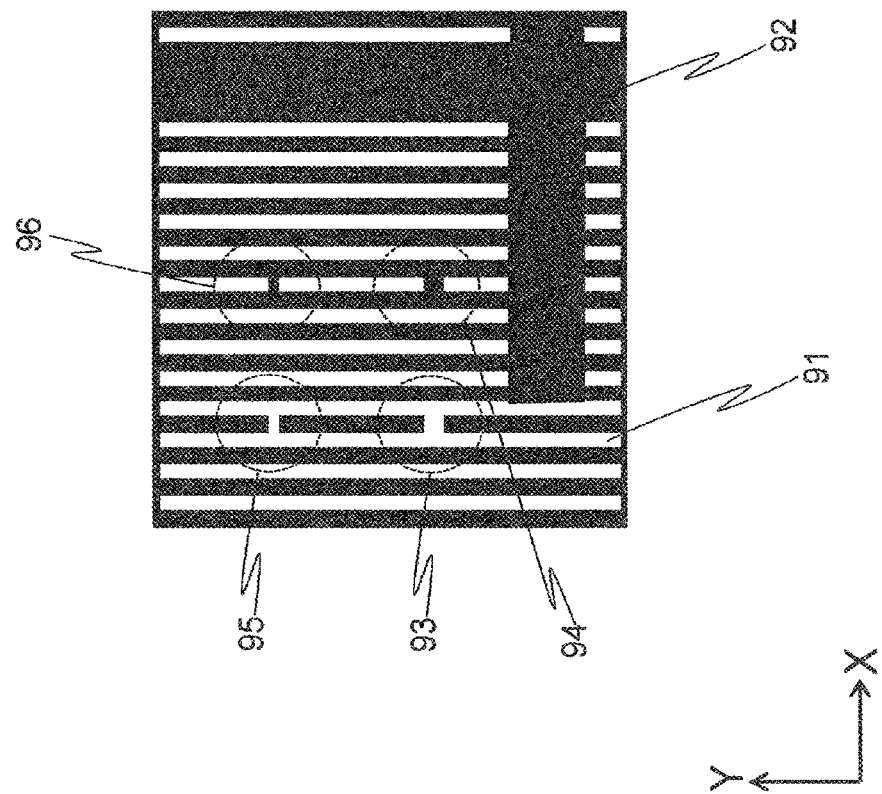
FIG. 20 is a view for illustrating a programmed defect provided in the alignment mark area according to the second embodiment.

FIG. 20 is one example the alignment mark area according to the present embodiment, and an extended plan view of a part of the alignment mark area. In FIG. 20, the mark 92 having a cross shape which can be used as an alignment mark, is formed by utilizing a difference of a contrast value between an area (white area) in which the fine line-and-space pattern 91 as the second pattern is provided, and an area (black area) in which the matrix 83 of the template is seen because the line-and-space pattern 91 is not provided. One straight line parallel to the Y-axis of the two straight lines comprising the cross shape of the mark 82, is longer than the other straight line parallel to the X-axis.

The programmed defects 93, 94, 95, and 96 are provided in the second pattern 91. Referring to FIG. 20, the programmed defects 93 and 95 simulate the bridge pattern defect. The programmed defects 94 and 96 simulate the broken pattern defect. Further, the size of the programmed defects 93 and 94 is equal to a line width of the first pattern. On the other hand, the size of programmed defects 95 and 96 is half the size of the line width of the first pattern. In the present embodiment it is preferable that a plurality of programmed defects having a different kind, shape, and/or dimension are provided, as mentioned above. The optimum value of the focus offset is changed depending on the kind, shape, and/or dimension of the defect, therefore, when plural programmed defects having different types, shapes, and dimensions of the defect are provided in one alignment mark, the optimum value of the focus offset can be determined as a whole defect to enhance the inspection accuracy.

The inspection method according to the present embodiment is the same as the first embodiment with the exception of the use of the programmed defect formed in the alignment mark area for adjusting the focus offset value, and the acquisition of the direction of the pattern to be inspected by the alignment mark. That is, the inspection method of the present embodiment is performed according to the steps S1 to S6 as shown in FIG. 8, and these steps are performed using the inspection apparatus 100 of FIG. 9. For example, in S4, the rotation angle (Faraday rotation angle θ) of the polarization plane of light by the Faraday rotator 204 is determined when the light quantity scattered by the edge roughness, to be incident to the sensor 207 is minimized among the light emitted from the light source 201, in the inspection apparatus 100, and irradiated on the template 2. In the present embodiment, by providing the simulated edge roughness defect in the alignment mark area, the condition for removing the light-dark unevenness scattered by the edge roughness, that is, the Faraday rotation angle θ for minimizing the light quantity scattered by the edge roughness and incident on the sensor 207, can be obtained from the optical image. The optical image used in the focus offset adjusting step (S3) can be used as the above-mentioned optical image.

As mentioned above, in the present embodiment, the programmed defect is provided in the alignment mark area, further, the alignment mark has the characterization reflecting the direction of the pattern to be inspected. That is, in the present embodiment, as the alignment mark area has the function of the focus offset adjusting pattern area according to the present embodiment, it is not necessary to provide that the focus offset adjusting pattern area. Accordingly, the scribe line area of the template can be effectively utilized.

Further, the focus offset value is adjusted using the second pattern, the third pattern, and the programmed defect provided in the alignment mark area, thereby the inspection can always be performed under the state of optimum focus offset. As a result, the reliability of the inspection result can be enhanced.

Further, as the alignment mark has a shape reflecting the direction of the pattern to be inspected, the direction of the pattern to be inspected can easily be obtained when the optimum value of the focus offset is obtained. Therefore, the optical image can be acquired at the optimum focal position by matching the direction of the pattern during the acquisition of the optical image to the direction of the pattern having the above-mentioned shape.

Third Embodiment

In the first embodiment, the second pattern in which the programmed defects are provided, and the third pattern for detecting the direction of the pattern to be inspected, are provided in the focus offset adjusting pattern area. Further, in the first embodiment, the inspection method includes a step for adjusting the focus offset value after the direction of the pattern to be inspected is obtained, and a step for determining the rotation angle of the Faraday rotator.

In the inspection method of the first embodiment, the focus offset value is adjusted so as to be the optimum focus offset value for detecting a defect by maximizing the signal-to-noise (S/N) ratio of the image signal. The rotation angle of the Faraday rotator is determined so as to remove the light-dark unevenness caused by the edge roughness.

On the other hand, in the inspection method according to the third embodiment, a new evaluation scale considering the intensity of the signal of the defect, and the background noise caused by the edge roughness, is introduced. Then, the optical image of the inspection target including the programmed defect is estimated according to the new evaluation scale. Thereby, the adjustment of the optimum focus offset value can be performed with the determination of the rotation angle of the Faraday rotator in the preliminary inspection process. Then, in the inspection process after the preliminary inspection process, the existence of a defect is determined based on the optical image of the pattern to be inspected, in the same manner as the first embodiment.

The inspection target according to the present embodiment is the same as the inspection target according to the first embodiment as shown in FIGS. 1 to 7, etc. That is, the inspection target according to the present embodiment includes the alignment mark area in the scribe line area which becomes the scribe line, provided in the outer periphery portion of the area in which the first pattern is provided. The second pattern and the third pattern are provided in any area of the scribe line area except the alignment mark area.

The inspection target as shown in FIGS. 16 to 20, etc., according to the second embodiment, can be the inspection target in the present embodiment. That is, the inspection target according to the present embodiment includes the alignment mark area in the scribe line area which becomes the scribe line provided to the outer periphery portion of the area in which the first pattern is provided. The alignment mark area includes the area in which the second pattern is disposed, and the area in which the second pattern is not disposed, for forming the alignment mark by the difference of the contrast between the area in which the second pattern is not disposed, and the area in which the second pattern is disposed. The third pattern can also be the alignment mark.

Therefore, in the inspection target according to the present embodiment, a plurality of defects of the same type and with different dimensions can be provided in the same manner as the first and second embodiments.

The inspection apparatus 100 shown in FIG. 9 is used in the present embodiment in the same manner as in the first embodiment.

The optical system of the inspection apparatus 100 which is used in the present embodiment, includes a polarization beam splitter 202, a half-wavelength plate 203, a Faraday rotator 204, and an objective lens 205. As mentioned above, after the focus offset is adjusted, the light emitted from the light source 201 is reflected by the polarization beam splitter 202, and transmitted through the half-wavelength plate 203, the Faraday rotator 204, and the objective lens 205. As a result, the light from the light source 201 is changed to the light having the polarization plane of the angle except an angle in the range of between −5 degrees and 5 degrees, and 85 degrees and 95 degrees, for example, and is illuminated to the repetitive direction of the above-mentioned first pattern. Then, the light reflected by the template 2 is transmitted through the objective lens 205, half-wavelength plate 203, the Faraday rotator 204, and the polarization beam splitter 202, the light is then incident to the sensor 207 to acquire the optical image of the programmed defect.

The template 2 mentioned in the first embodiment, as the inspection target in the present embodiment, is inspected by the inspection apparatus 100 as follows. Components of the inspection target and inspection apparatus, etc. which are common to the first embodiment are applied herein with the same reference numbers and thus a repeated description is omitted.

Figure 28:
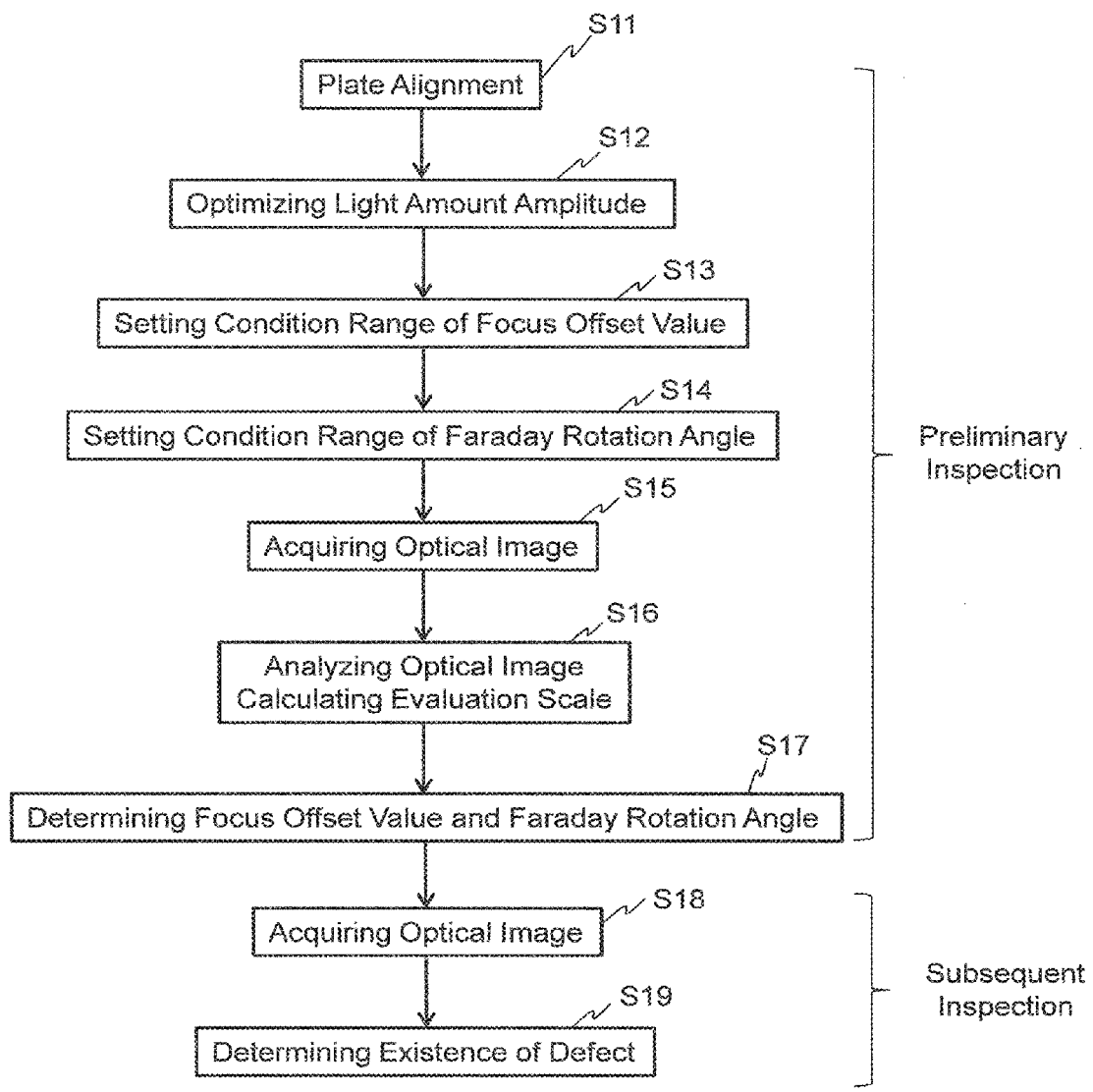
FIG. 28 is a flowchart illustrating the inspection method according to the third embodiment.

FIG. 28 is a flowchart illustrating the inspection method according to the present embodiment. In FIG. 28, the inspection process for determining the existence of a defect based on the optical image of the inspection target, corresponds to S18 and S19, and S11 to S17 corresponds to the preliminary inspection process, which is performed before the inspection process.

In the inspection method according to the present embodiment, firstly, the template 2 is positioned on the table 1 of the inspection apparatus 100, and then the plate alignment is performed (S11) as shown in FIG. 28, in the same manner as S1 of the inspection method shown in FIG. 8 according to the first embodiment.

Next, as shown in FIG. 28, the amplitude of the light quantity of the sensor 207 for acquiring the optical image of the template 2 is optimized (S12), in the same manner as S2 of the inspection method shown in FIG. 8 according to the first embodiment.

Next, in the inspection method according to the present embodiment, as shown in FIG. 28, the range of the focus offset for acquiring the optical image of the programmed defect is set (S13).

Specifically, the presumed range that includes the optimum focus offset, is determined. For example, the range between −0.5 µm and 0.5 µm is determined. Then, the optimum focal position is set as the middle of the range, as a result, the range between −0.5 µm and 0.5 µm can be set as the range of the focus offset.

Next, as shown in FIG. 28, the range of the rotation angle of the Faraday rotator 204 for acquiring the optical image of the programmed defect is set. As a result, corresponding to the rotation angle of the Faraday rotator 204, the range of the rotation angle (Faraday rotation angle θ) of the polarization plane of the light transmitted through the Faraday rotator 204 can be set (S14).

Specifically, regarding the Faraday rotator 204 of the inspection apparatus 100 shown in FIG. 9, the condition range, including the estimated optimum rotation, is obtained. For example, the fluctuation range is determined to be between −5 degrees and 5 degrees. An angle of 45 degrees to the repetitive direction of the repetitive pattern formed in the template 2 is set as a middle value, and then a range between −5 degrees and 5 degrees, can be set as the condition value of the rotation angle of the Faraday rotator 204. That is, a range between 40 degrees and 50 degrees to the above-mentioned repetitive direction can be set as the condition range of the rotation angle of the Faraday rotator 204. As a result, the condition range of the rotation angle (Faraday rotation angle θ) of the polarization plane of the light transmitted through the Faraday rotator 204 can be set in the same manner, depending on the condition range of the rotation angle of the Faraday rotator 204.

Next, as shown in FIG. 28, while the conditions of the focus offset are changed in the predetermined range set in S13, and the rotation angle of the Faraday rotator 204 is changed in the predetermined range set in S14, the optical image of the programmed defect which is disposed in the second pattern, is acquired (S15).

That is, regarding the focus offset, the condition of the focus offset is changed, for example, in the range between −0.5 µm and 0.5 µm, with the focal position as the middle value. In this case, the condition of the focus offset can be changed by changing the focal distance between the imprint surface of the template 2 and the objective lens 205.

Further, the rotation angle of the Faraday rotator 204 is changed in the range between −5 degrees and 5 degrees, with the angle of 45 degrees to the repetitive direction of the repetitive pattern of the above-mentioned template 2, as the middle value. That is, the rotation angle of the Faraday rotator 204 is changed in the range between 40 degrees and 50 degrees to the above-mentioned repetitive direction. In this case, the rotation angle of the Faraday rotator 204 can be changed by controlling an intensity of an applied magnetic field to the Faraday rotator 204. Then, the rotation angle (Faraday rotation angle θ) of the polarization plane of the light transmitted through the Faraday rotator 204 can be changed depending on the change of the rotation angle of the Faraday rotator 204. As a result, the condition of the Faraday rotation angle can be changed.

Regarding the acquisition of the optical image of the programmed defect in S15 shown in FIG. 28, for example, a plurality of the conditions of the focus offset are selected in the above-mentioned set range, and a plurality of the conditions of the Faraday rotation angle are selected in the above-mentioned set range. In this case, for example, five conditions may be selected as the focus offset conditions, and further five conditions may be selected as the Faraday rotation angle conditions.

In the acquisition of the optical image of the programmed defect in S15 shown in FIG. 28, the optical images of the programmed defect corresponding to all conditions are acquired. That is, in the above-mentioned case, the optical image of the programmed defect disposed in the second pattern formed in the template 2, can be acquired under all conditions consisting of the twenty five conditions (5 conditions×5 conditions) according to the five conditions of the focus offset, and the five conditions of the Faraday rotation angle.

As a method for selecting the five conditions regarding the focus offset, for example, the five conditions with an equal interval such as five conditions consisting of "focal position −0.5 μm", "focal position −0.25 μm", "focal position", "focal position+0.25 μm", and "focal position+0.5 μm", may be set.

Further, as a method for selecting five conditions regarding the rotation angle of the Faraday rotator, for example, the five conditions with an equal interval such as the five conditions consisting of "an angle of 40 degrees to the repetitive direction", "an angle of 42.5 degrees to the repetitive direction", "an angle of 45 degrees to the repetitive direction", "an angle of 47.5 degrees to the repetitive direction", and "an angle of 50 degrees to the repetitive direction", may be set.

The above-mentioned conditions for the acquisition of the optical image are not limited to the twenty five conditions, consisting of the five conditions of the focus offset, and the five conditions of the rotation angle of the Faraday rotator 204. For example, the conditions of the acquisition of the optical image may be nine conditions (3 conditions×3 conditions) consisting of the three conditions of the focus offset, and the three conditions of the rotation angle of the Faraday rotator 204. Further, the conditions of the acquisition of the optical image may be twenty conditions (4 conditions×5 conditions) consisting of the four conditions of the focus offset, and the five conditions of the rotation angle of the Faraday rotator 204. That is, the number of the focus offset conditions may be different to the number of the condition of the rotation angle of the Faraday rotator 204.

Next, as shown in FIG. 28, the condition for the inspection for determining an existence of a defect is extracted by analyzing each image acquired under the different conditions, and comparing those images with each other (S16). That is, in S16, all acquired images are analyzed, and then a ratio of signal-to-noise (S/N) is calculated as a new evaluation scale. In this case, the ratio of signal-to-noise (S/N) calculated in S16, is different to the ratio of signal-to-noise (S/N) to be used as a scale for obtaining the optimum focal distance in S3 of the inspection method according to the first embodiment as mentioned above. Accordingly, the ratio of signal-to-noise (S/N) calculated in S16 is conveniently called a second signal-to-noise (S/N) ratio below. The condition for the inspection is extracted based on the calculated second signal-to-noise (S/N) ratio.

The analysis of the optical image, and the calculation for the above-mentioned second signal-to-noise (S/N) ratio can be performed using the image processing circuit 108 in the inspection apparatus 100 as follows.

For example, in the step (S15) for acquiring the optical image of the programmed defect provided in the second pattern formed in the template 2, the optical images are acquired under the nine conditions consisting of the three conditions of the focus offset, and the three conditions of the rotation angle of the Faraday rotator 204. In all images acquired under the nine conditions, for example, the programmed defect disposed in the second pattern, appears as a white spot in the optical image as well as the defect in the area D2 shown in FIG. 12. Further, depending on the condition of the focus offset, and/or the condition of the Faraday rotation angle, for example, the background noise caused by the edge roughness appears as the light-dark unevenness in which the dark gray area and the light gray area are mixed by variation of the gray level, as well as the defect in the area D3 shown in FIG. 12, with the white spot caused by the programmed defect.

Among all images acquired under the above-mentioned nine conditions, a defect image of which the contrast value between the white spot caused by the programmed defect, and the background of the white spot is high, and the background noise caused by the edge roughness is restrained, is extracted as the image acquired under the optimum condition. Then, the condition for acquiring the extracted image of the defect, that is, the focus offset condition and the condition of the rotation angle of the Faraday rotator which is the Faraday rotation angle, are determined as the condition for acquiring an optical image in the inspection process.

The extraction of the condition for acquiring the optical image in the inspection is performed by analyzing all images acquired under the nine conditions, and calculating the ratio of signal-to-noise (S/N) regarding the above-mentioned second image signal. Specifically, the extraction can be performed as follows.

Firstly, each acquired image is analyzed, and then the signal intensity of the programmed defect disposed in the second pattern in the template, that appears as a white spot, is calculated as mentioned above.

Figure 29:
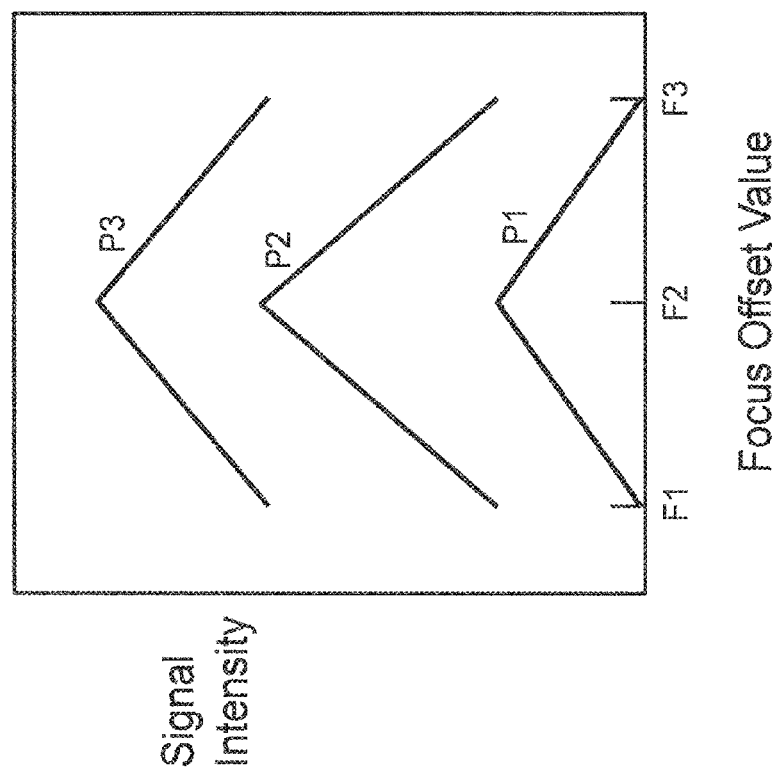
FIG. 29 is a graph illustrating the comparison of the calculation result of the signal intensity.

FIG. 29 is a graph illustrating the comparison of the calculation result of the signal intensity.

As shown in FIG. 29, the vertical axis of the graph corresponds to a signal intensity of the optical image of the programmed defect that appears as a white spot, and the horizontal axis of the graph corresponds to a condition range of the focus offset. In this case, the three conditions (F1, F2, and F3) are set as the specific condition of the focus offset, and the three conditions (P1, P2, and P3) are set as the specific condition of the rotation angle of the Faraday rotator 204. Then, the signal intensities of the optical image of the programmed defect acquired under the nine conditions are plotted on the graph. Thereby, three types of line graphs which include estimation results of all images acquired under the nine conditions, corresponding to the three conditions (P1, P2, and P3) of the rotation angles of the Faraday rotator 204, can be obtained.

In FIG. 29, the signal intensity corresponding to each line of the graph illustrates the degree of the brightness of the white spot caused by the programmed defect. In the case where the rotation angle of the Faraday rotator 204 is P3, FIG. 29 shows that the intensity of the defect signal is high, and therefore the white spot caused by the programmed defect is easily seen with a high precision.

Next, the nine types of images are analyzed respectively, and then the intensity of the background noise caused by the edge roughness is calculated. In this case, the intensity of the background noise caused by the edge roughness is obtained by calculating the degree of the fluctuation of the gray level of the surrounding area except the white spot caused by the programmed defect.

Figure 30:
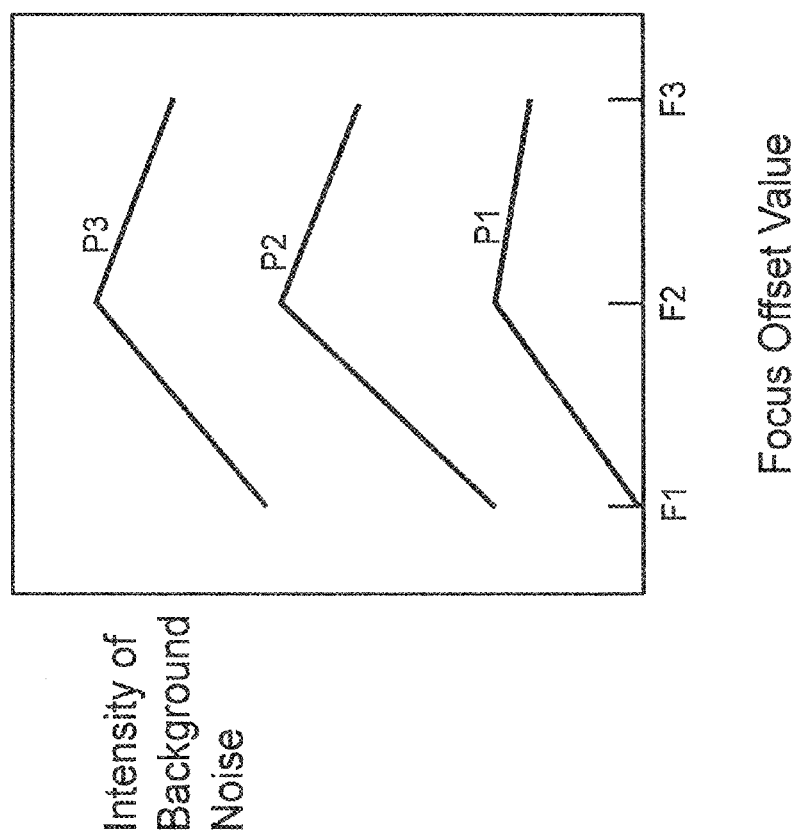
FIG. 30 is a graph illustrating the comparison of the calculation result of the signal intensity of the background noise caused by the edge roughness.

FIG. 30 is a graph illustrating the comparison of the calculation result of the signal intensity of the background noise caused by the edge roughness.

As shown in FIG. 30, the vertical axis of the graph corresponds to an intensity of the background noise, and the horizontal axis of the graph corresponds to a condition range of the focus offset. In this case, the three conditions (F1, F2, and F3) are set as the specific condition of the focus offset, and the three conditions (P1, P2, and P3) are set as the specific condition of the rotation angle of the Faraday rotator 204. Then, the signal intensities of the optical image of the programmed defect acquired under the nine conditions are plotted on the graph. Thereby, three types of line graphs which include estimation results of all images acquired under the nine conditions, corresponding to the three conditions (P1, P2, and P3) of the rotation angles of the Faraday rotator 204, can be obtained.

In this case, the intensity of the background shown in FIG. 30 illustrates the degree of background noise caused by the edge roughness. Therefore, FIG. 30 shows that the intensity of the background noise is strongest in the case where the rotation angle of the Faraday rotator 204 is P3. On the other hand, FIG. 30 shows that the intensity of the background noise is weakest in the case where the rotation angle of the Faraday rotator 204 is P2.

According to the calculation result shown in FIG. 29, the condition that the rotation angle of the Faraday rotator 204 is P3, is an optimum condition because it makes the white spot caused by the programmed defect to be at the highest brightness. However, considering this in conjunction with the calculation result shown in FIG. 30, in the condition that the rotation angle of the Faraday rotator 204 is P3, it is actually difficult to determine an existence of a defect because the intensity of the background noise is strong.

In the present embodiment, a new estimation scale including the intensity of the defect signal and the background noise caused by the edge roughness is calculated for use. Thereby, the effective estimation can be performed to the optical image of the inspection target including the programmed defect.

For example, a ratio of the second signal-to-noise (S/N) is calculated by dividing the signal intensity of the programmed defect shown in FIG. 29 by the signal intensity of the background noise caused by the edge roughness shown in FIG. 30. Then, using the ratio of the second signal-to-noise (S/N) as the new estimation scale, the optical image of the programmed defect disposed in the second pattern of the inspection target is estimated.

Figure 31:
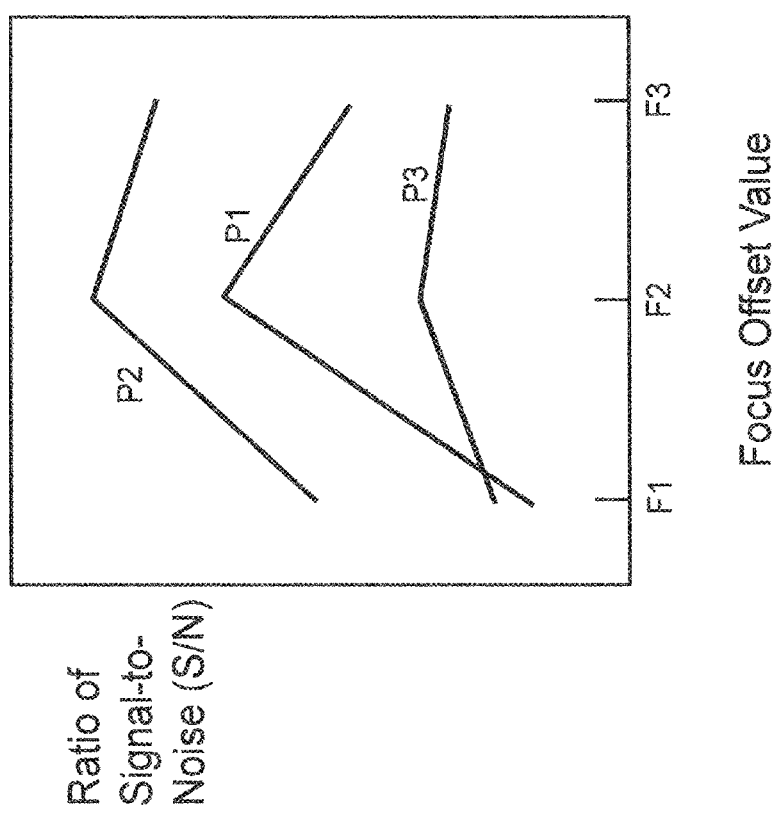
FIG. 31 is a graph illustrating the comparison of the calculation result of the ratio of the second signal-to-noise (S/N).

FIG. 31 is a graph illustrating the comparison of the calculation result of the ratio of the second signal-to-noise (S/N).

As shown in FIG. 31, the vertical axis of the graph corresponds to the above-mentioned ratio of the second signal-to-noise (S/N), and the horizontal axis of the graph corresponds to a condition range of the focus offset. In this case, the three conditions (F1, F2, and F3) are set as the specific condition of the focus offset, and the three conditions (P1, P2, and P3) are set as the specific condition of the rotation angle of the Faraday rotator 204. Then, the ratio of the second signal-to-noise (S/N) obtained under the nine conditions, are plotted on the graph. Thereby, three types of line graphs which include estimation results of all images acquired under the nine conditions, corresponding to the three conditions (P1, P2, and P3) of the rotation angles of the Faraday rotator 204, can be obtained.

The ratio of the second signal-to-noise (S/N) shown in FIG. 31 illustrates the degree of visibility of the white spot caused by the programmed defect. In the case where the rotation angle of the Faraday rotator 204 is P2, FIG. 31 shows that the ratio of the second signal-to-noise (S/N) is high. Further, FIG. 31 shows that the ratio of the second signal-to-noise (S/N) is high in the case where the condition of the focus offset is F2.

As mentioned above, decrease of the background noise caused by the edge roughness in addition to the strength of the intensity of the defect signal, is effectively applied in the estimation of the optical image of the programmed defect. As a result, the condition that the rotation angle of the Faraday rotator is P2, and the focus offset condition is F2, is an optimum condition for acquiring an optical image. That is, according to this condition, the contrast value between the white spot caused by the programmed defect, and the background of the white spot, is high, and further the background noise caused by the edge roughness is suppressed. Accordingly, it can be determined that the condition of the rotation angle of the Faraday rotator is P2, and the focus offset condition is F2, is the most effective condition for the detection of a defect of the inspection target.

Next, in the inspection method according to the present embodiment, the condition of the focus offset and the above-mentioned condition for an optical image regarding the Faraday rotation angle as a rotation angle of the Faraday rotator 204, is determined as the most effective condition for detecting a defect of the inspection target (S17).

Namely, the condition for acquiring that the rotation angle of the Faraday rotator 204 is P2, and the focus offset condition is F2, as shown in FIG. 31, is determined as a condition for acquiring an optical image in the inspection process.

Next, as shown in FIG. 28, the optical image of the template 2 is acquired (S18) in the same manner as S5 of the inspection method in FIG. 8 according to the first embodiment. After that, an existence of a defect is determined based on the optical image of the template 2 (S19) in the same manner as S6 of the inspection method according to the first embodiment.

As mentioned above, the programmed defect is disposed in the template according to the present embodiment. Further, by deriving a new estimation scale wherein the intensity of the defect signal and the intensity of the background noise caused by the edge roughness are taken into account, the condition for acquiring an optical image of the inspection target including the programmed defect becomes a more preferable condition for acquiring the optical image.

According to the inspection method of the present embodiment, the focus offset is adjusted using the above-mentioned programmed defect. Therefore, the inspection can always be performed under the optimum focus offset. Further, the reliability of the inspection result can be enhanced as a result.

Furthermore, using the programmed defect, the condition that removes the bright and dark unevenness caused by the light scattered by the edge roughness, namely, the condition in which the Faraday rotation angle θ is obtained when the light quantity that is scattered by the edge roughness and is incident to the sensor, becomes minimum. Thereby, the inspection of the pattern finer than the resolution limit of the optical system can be accurately performed. Specifically, the inspection for determining an existence of a bridge pattern defect and/or broken pattern defect can be performed by acquiring an optical image in which the bright and dark unevenness caused by the light scattered by the edge roughness is removed.

In the above-mentioned examples according to the third embodiment, the template 2 is inspected using the inspection apparatus 100 in the same manner as the first embodiment. Further, in the third embodiment, the inspection target mentioned in the second embodiment can be inspected using the inspection apparatus 100.

The present invention is not limited to the embodiment described and can be implemented in various ways without departing from the spirit of the invention.

For example, in the third embodiment, the first pattern and the second pattern are line-and-space patterns. However, in the third embodiment, another pattern except the line-and-space pattern, for example, a rectangular pattern or hole pattern, can be used. In this case, a bridge pattern defect should be a defect in which rectangles or holes are in contact with each other. On the other hand, in a broken pattern defect, a part of rectangular or hole pattern is lacking.

In the rectangular pattern and hole pattern, in the case where the dimension between one rectangle and the neighboring rectangle along the X-direction, or the dimension between one hole and the neighboring hole along the X-direction, is different to the dimension in the Y-direction, it is necessary that the direction of the inspection target when the focus offset is adjusted corresponds to the direction of the inspection target when the optical image is acquired in the inspection.

Figure 21:
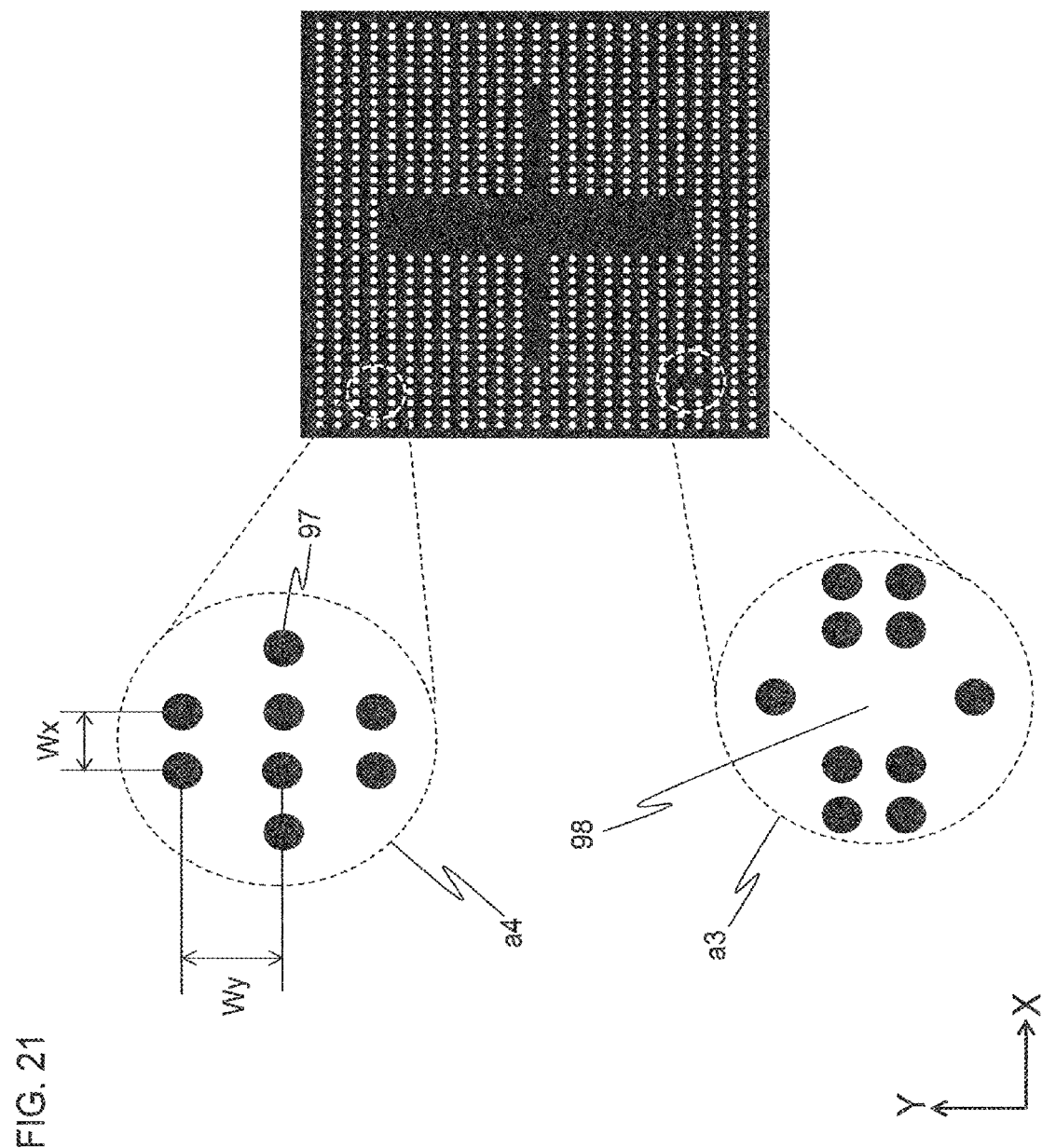
FIG. 21 is another example of the alignment mark area according to the second embodiment.

FIG. 21 illustrates one example of the second pattern 97, in which the second pattern 97 is a hole pattern, and in which the alignment mark is cross-shaped. In the area a3, the programmed defect 98 simulating a broken pattern defect in which the hole pattern is lacking, is disposed.

Further, in the hole pattern, the dimension Wx between the holes along the X-direction, is different to the dimension Wy between the holes along the Y-direction. Therefore, the optimum value of the focus offset is different depending on the direction of the hole patterns. That is, the optimum value of the focus offset when the template is positioned on the table, so that the dimension Wx between the holes along the X-direction is larger than the dimension Wy between the holes along the Y-direction, is different to the optimum value of the focus offset when the template is positioned on the table, so that the dimension Wy between the holes along the Y-direction is larger than the dimension Wx between the holes along the X-direction. Accordingly, for example, as shown in FIG. 21, the width between two lines consisting of the cross-shaped mark is changed so that the direction of the thicker line, corresponds to the direction in which the dimension Wy between the holes along the Y-direction is larger than the dimension Wx between the holes along the X-direction in the second pattern 97. Thereby, the direction of the inspection target, when the optimum focus offset is obtained, is easily obtained. Therefore, an optical image is acquired at the optimum focal position by corresponding the direction when the optimum focal offset is obtained to the direction when the optical image is acquired.

However, the second pattern does not necessarily simulate the first pattern. In the case that the first pattern differs from the second pattern in the dimension, there is the possibility that the optimum value of the focus offset obtained using the programmed defect in the second pattern (or the optimum value of the Faraday rotation angle θ) is not matched with the optimum value in the defect of the first pattern. Specifically, in the case that the line width or the distance between the lines varies in the line-and-space pattern, a hole diameter of the hole pattern or the distance between the holes varies, or the location of the alignment mark differs from the area to be inspected in a duty ratio defined by a width and a pitch of each line in the line-and-space pattern, the optimum value of the focus offset obtained using the programmed defect or the optimum value of the Faraday rotation angle θ is not matched with the optimum value in the defect of the first pattern. In such cases, preferably a coefficient used to convert or correct the optimum value of the second pattern into the optimum value of the first pattern is prepared.

The present invention can also be applied to a substrate other than a template substrate, for example, a mask substrate. In the above embodiments, by way of example, the pattern provided in the template is set to the inspection target, and the alignment mark is provided in the template. In the case that the pattern provided in the mask is set to the inspection target, the alignment mark of the embodiments may be arranged flush with the pattern that is of the inspection target on the mask substrate. Therefore, the defect of the mask pattern finer than the resolution limit of the optical system in the inspection apparatus can accurately be detected by properly adjusting the focus offset.

The above description of the embodiments has not specified apparatus constructions, control methods, etc., which are not essential to the description of the invention, since any suitable apparatus construction, control methods, etc. can be employed to implement the invention. Further, the scope of this invention encompasses all inspection methods, substrates, template substrates, and focus offset methods employing the elements of the invention and variations thereof, which can be designed by those skilled in the art.

Further features of the present invention may be summarized as follows.

According to one aspect of the present invention, an inspection method for inspecting a substrate to detect the existence of a defect using an optical image obtained by irradiating a substrate with light emitted from a light source through an optical unit, and causing the light reflected by the substrate to be incident to a sensor through the optical unit includes adjusting a focus offset value such that a focal distance for setting the signal-to-noise (S/N) ratio of a programmed defect to the maximum level, is obtained in an optical image of the programmed defect by acquiring the optical image while changing a focal distance between the surface in which a first pattern is provided and the optical unit. The substrate includes the first pattern consisting of a repetitive pattern that is finer than the resolution limit of the optical unit; a second pattern arranged on the same plane as the first pattern, having the same direction as the first pattern, and consisting of a repetitive pattern that is finer than the resolution limit of the optical unit; a programmed defect disposed in the second pattern, finer than the resolution limit of the optical unit; and a third pattern arranged on the same plane as the first pattern, having a shape reflecting the direction of the first pattern, not finer than the resolution limit of the optical unit. The existence of a defect of the first pattern is detected by acquiring an optical image of the first pattern after the focus offset is adjusted.

Further, according to another aspect of the present invention, the substrate includes an alignment mark area in a scribe line area arranged in the outer periphery portion of the area in which the first pattern is disposed. The second pattern and the third pattern are disposed in any area of the scribe line area except the alignment mark area.

Further, according to another aspect of the present invention, the substrate includes an alignment mark area in a scribe line area arranged in the outer periphery portion of the area in which the first pattern is disposed. The alignment mark area includes an area comprising the second pattern, and an area in which the second pattern is not disposed, for forming the alignment mark by the difference of the contrast between the area in which the second pattern is not disposed, and the area in which the second pattern is disposed. The third pattern also functions as the alignment mark.

Further, according to another aspect of the present invention, the programmed defect includes a plurality of defects of the same type and with different dimensions Further, according to another aspect of the present invention, further the focus offset value, obtained from the optical image of the programmed defect disposed in the second pattern, is optimized for the first pattern when the first pattern differs from the second pattern in size or when the first pattern differs from the second pattern in a duty ratio defined by a width and a pitch of each line while both the first pattern and the second pattern are a line-and-space pattern.

Further, according to another aspect of the present invention, the optical unit includes a polarization beam splitter, a half-wavelength plate, a Faraday rotator, and an objective lens. After the focus offset value is adjusted, light is emitted from the light source, and then is reflected by the polarization beamsplitter, and then is transmitted through the half-wavelength plate, the Faraday rotator, and the objective lens. Then the substrate is irradiated with the light having a polarization plane of an angle except an angle within a range of an angle equal to or larger than −5 degrees and an angle equal to or smaller than 5 degrees, and a range of an angle equal to or larger than 85 degrees and an angle equal to or smaller than 95 degrees with respect to a repetitive direction of a repetitive pattern of the first pattern. Then the light reflected by the substrate is transmitted through the objective lens, the half-wavelength plate, the Faraday rotator, and the polarization beamsplitter. An optical image of the programmed defect is acquired by causing the light to be incident to the sensor. A gradation value is obtained in each pixel with respect to the optical image of the programmed defect. After that, (1) a rotation angle of the polarization plane of the light rotated by the Faraday rotator for minimizing a standard deviation of the gradation value, or (2) a rotation angle for minimizing a value which is obtained by dividing the standard deviation of the gradation values of a plurality of optical images of the programmed defect obtained by changing the rotation angle, by a square root of an average gradation value obtained from the gradation values, is obtained. A magnetic field is applied to the Faraday rotator such that the obtained rotation angle is achieved. An optical image of the first pattern is acquired while the magnetic field is applied to the Faraday rotator. The existence of a defect of the first pattern is detected using the optical image of the first pattern. The first pattern and the second pattern are a line-and-space pattern. The programmed defect includes at least one of a pattern bridge defect in which lines are short-circuited with each other, a broken pattern defect in which the line is disconnected, and a defect caused by an edge roughness.

According to another aspect of the present invention, in an inspection method for inspecting a substrate to detect the existence of a defect using an optical image obtained by irradiating a substrate with light emitted from a light source through an optical unit, and causing the light reflected by the substrate to be incident to a sensor through the optical unit, the substrate includes a first pattern consisting of a repetitive pattern finer than the resolution limit of the optical unit; a second pattern arranged on the same plane as the first pattern, having the same direction as the first pattern, and consisting of a repetitive pattern finer than the resolution limit of the optical unit; a programmed defect disposed in the second pattern, finer than the resolution limit of the optical unit; and a third pattern arranged on the same plane as the first pattern, having a shape reflecting the direction of the first pattern, not finer than the resolution limit of the optical unit. The first pattern and the second pattern are a line-and-space pattern. The programmed defect includes at least one of a pattern bridge defect in which lines are short-circuited with each other, a broken pattern defect in which the line is disconnected, and a defect caused by an edge roughness. The optical unit includes a polarization beam splitter, a half-wavelength plate, a Faraday rotator, and an objective lens, and is configured to acquire an optical image of the programmed defect, after a focus offset value is adjusted, emitting light from the light source, reflecting the light by the polarization beamsplitter, transmitting the light through the half-wavelength plate, the Faraday rotator, the objective lens, irradiating the substrate with the light having a polarization plane of an angle except an angle within a range of an angle equal to or larger than −5 degrees and an angle equal to or smaller than 5 degrees, and a range of an angle equal to or larger than 85 degrees and an angle equal to or smaller than 95 degrees with respect to a repetitive direction of a repetitive pattern of the first pattern, transmitting the light reflected by the substrate through the objective lens, the half-wavelength plate, the Faraday rotator, and the polarization beamsplitter, causing the light to be incident to the sensor. The inspection method includes setting a condition range of a focus offset value for adjusting the focus offset value. A condition range of an angle of the Faraday rotator is set for adjusting an angle with respect to the repetitive direction of the repetitive pattern of the first pattern. An optical image of the programmed defect is acquired under a plurality of conditions within the range of the condition range of a focus offset value while changing the condition of the focus offset value, and changing the condition of the angle of the Faraday rotator within the condition range of an angle of the Faraday rotator. The plurality of optical images are analyzed, and then an evaluation scale is calculated by dividing a signal intensity of either the pattern bridge defect or the broken pattern defect of the programmed defect by a signal intensity of noise caused by the edge roughness. The condition of the focus offset value and the condition of an angle of the Faraday rotator are extracted for acquiring an optical image of the programmed defect using the evaluation scale, and then the inspection condition of the focus offset value and the inspection condition of the angle of the Faraday rotator are determined for detecting the existence of a defect of the first pattern. An optical image of the first pattern is acquired according to the inspection condition of the focus offset value and the inspection condition of the angle of the Faraday rotator, and then the existence of a defect of the first pattern is detected.

Further, according to another aspect of the present invention regarding another inspection method for inspecting a substrate to detect the existence of a defect, the substrate includes an alignment mark area in a scribe line area arranged in the outer periphery portion of the area in which the first pattern is disposed. The second pattern and the third pattern are disposed in any area of the scribe line area except the alignment mark area.

Further, according to another aspect of the present invention, an inspection method, the programmed defect includes a plurality of defects of the same type and with different dimensions.

What is claimed is:

1. An inspection method for inspecting a substrate to detect the existence of a defect using an optical image obtained by irradiating a substrate with light emitted from a light source through an optical unit, and causing the light reflected by the substrate to be incident to a sensor through the optical unit,
   wherein the substrate includes a first pattern consisting of a repetitive pattern that is finer than the resolution limit of the optical unit;
   a second pattern arranged on the same plane as the first pattern, having the same direction as the first pattern, and consisting of a repetitive pattern that is finer than the resolution limit of the optical unit;
   a programmed defect disposed in the second pattern, finer than the resolution limit of the optical unit; and
   a third pattern arranged on the same plane as the first pattern, having a shape reflecting the direction of the first pattern, not finer than the resolution limit of the optical unit, the inspection method comprising:
   adjusting a focus offset value such that a focal distance for setting the signal-to-noise ratio of the programmed defect to the maximum level, is obtained in an optical image of the programmed defect by acquiring the optical image while changing a focal distance between the surface in which the first pattern is provided and the optical unit;
   detecting the existence of a defect of the first pattern by acquiring an optical image of the first pattern after the focus offset is adjusted.

2. The inspection method according to claim 1,
   wherein the substrate comprises an alignment mark area in a scribe line area arranged in the outer periphery portion of the area in which the first pattern is disposed; and
   wherein the second pattern and the third pattern are disposed in any area of the scribe line area except the alignment mark area.

3. The inspection method according to claim 1,
   wherein the substrate comprises an alignment mark area in a scribe line area arranged in the outer periphery portion of the area in which the first pattern is disposed;
   wherein the alignment mark area includes an area comprising the second pattern, and an area in which the second pattern is not disposed, for forming the alignment mark by the difference of the contrast between the area in which the second pattern is not disposed, and the area in which the second pattern is disposed; and
   wherein the third pattern also functions as the alignment mark.

4. The inspection method according to claim 1,
   wherein the programmed defect comprises a plurality of defects of the same type and with different dimensions.

5. The inspection method according to claim 1, further comprising optimizing the focus offset value, obtained from the optical image of the programmed defect disposed in the second pattern, for the first pattern when the first pattern differs from the second pattern in size or when the first pattern differs from the second pattern in a duty ratio defined by a width and a pitch of each line while both the first pattern and the second pattern are a line-and-space pattern.

6. The inspection method according to claim 2, further comprising optimizing the focus offset value, obtained from the optical image of the programmed defect disposed in the second pattern, for the first pattern when the first pattern differs from the second pattern in size or when the first pattern differs from the second pattern in a duty ratio defined by a width and a pitch of each line while both the first pattern and the second pattern are a line-and-space pattern.

7. The inspection method according to claim 3, further comprising optimizing the focus offset value, obtained from the optical image of the programmed defect disposed in the second pattern, for the first pattern when the first pattern differs from the second pattern in size or when the first pattern differs from the second pattern in a duty ratio defined by a width and a pitch of each line while both the first pattern and the second pattern are a line-and-space pattern.

8. The inspection method according to claim 4, further comprising optimizing the focus offset value, obtained from the optical image of the programmed defect disposed in the second pattern, for the first pattern when the first pattern differs from the second pattern in size or when the first pattern differs from the second pattern in a duty ratio defined by a width and a pitch of each line while both the first pattern and the second pattern are a line-and-space pattern.

9. The inspection method according to claim 1, wherein the optical unit comprises a polarization beam splitter, a half-wavelength plate, a Faraday rotator, and an objective lens, further comprising:
   after the focus offset value is adjusted, emitting light from the light source, reflecting the light by the polarization beamsplitter, transmitting the light through the half-wavelength plate, the Faraday rotator, the objective lens, irradiating the substrate with the light having a polarization plane of an angle except an angle within a range of an angle equal to or larger than −5 degrees and an angle equal to or smaller than 5 degrees, and a range of an angle equal to or larger than 85 degrees and an angle equal to or smaller than 95 degrees with respect to a repetitive direction of a repetitive pattern of the first pattern, transmitting the light reflected by the substrate through the objective lens, the half-wavelength plate, the Faraday rotator, and the polarization beamsplitter, acquiring an optical image of the programmed defect by causing the light to be incident to the sensor;
   obtaining a gradation value in each pixel with respect to the optical image of the programmed defect, obtaining (1) a rotation angle of the polarization plane of the light rotated by the Faraday rotator for minimizing a standard deviation of the gradation value, or (2) a rotation angle for minimizing a value which is obtained by dividing the standard deviation of the gradation values of a plurality of optical images of the programmed defect obtained by changing the rotation angle, by a square root of an average gradation value obtained from the gradation values;
   applying a magnetic field to the Faraday rotator such that the obtained rotation angle is achieved;
   acquiring an optical image of the first pattern while the magnetic field is applied to the Faraday rotator; and
   detecting the existence of a defect of the first pattern using the optical image of the first pattern;

wherein the first pattern and the second pattern are a line-and-space pattern, and wherein the programmed defect comprises at least one of a pattern bridge defect in which lines are short-circuited with each other, a broken pattern defect in which the line is disconnected, and a defect caused by an edge roughness.

10. The inspection method according to claim 2, wherein the optical unit comprises a polarization beam splitter, a half-wavelength plate, a Faraday rotator, and an objective lens, further comprising:

after the focus offset value is adjusted, emitting light from the light source, reflecting the light by the polarization beamsplitter, transmitting the light through the half-wavelength plate, the Faraday rotator, the objective lens, irradiating the substrate with the light having a polarization plane of an angle except an angle within a range of an angle equal to or larger than −5 degrees and an angle equal to or smaller than 5 degrees, and a range of an angle equal to or larger than 85 degrees and an angle equal to or smaller than 95 degrees with respect to a repetitive direction of a repetitive pattern of the first pattern, transmitting the light reflected by the substrate through the objective lens, the half-wavelength plate, the Faraday rotator, and the polarization beamsplitter, acquiring an optical image of the programmed defect by causing the light to be incident to the sensor;

obtaining a gradation value in each pixel with respect to the optical image of the programmed defect, obtaining (1) a rotation angle of the polarization plane of the light rotated by the Faraday rotator for minimizing a standard deviation of the gradation value, or (2) a rotation angle for minimizing a value which is obtained by dividing the standard deviation of the gradation values of a plurality of optical images of the programmed defect obtained by changing the rotation angle, by a square root of an average gradation value obtained from the gradation values;

applying a magnetic field to the Faraday rotator such that the obtained rotation angle is achieved;

acquiring an optical image of the first pattern while the magnetic field is applied to the Faraday rotator; and detecting the existence of a defect of the first pattern using the optical image of the first pattern;

wherein the first pattern and the second pattern are a line-and-space pattern, and wherein the programmed defect comprises at least one of a pattern bridge defect in which lines are short-circuited with each other, a broken pattern defect in which the line is disconnected, and a defect caused by an edge roughness.

11. The inspection method according to claim 3, wherein the optical unit comprises a polarization beam splitter, a half-wavelength plate, a Faraday rotator, and an objective lens, further comprising:

after the focus offset value is adjusted, emitting light from the light source, reflecting the light by the polarization beamsplitter, transmitting the light through the half-wavelength plate, the Faraday rotator, the objective lens, irradiating the substrate with the light having a polarization plane of an angle except an angle within a range of an angle equal to or larger than −5 degrees and an angle equal to or smaller than 5 degrees, and a range of an angle equal to or larger than 85 degrees and an angle equal to or smaller than 95 degrees with respect to a repetitive direction of a repetitive pattern of the first pattern, transmitting the light reflected by the substrate through the objective lens, the half-wavelength plate, the Faraday rotator, and the polarization beamsplitter, acquiring an optical image of the programmed defect by causing the light to be incident to the sensor;

obtaining a gradation value in each pixel with respect to the optical image of the programmed defect, obtaining (1) a rotation angle of the polarization plane of the light rotated by the Faraday rotator for minimizing a standard deviation of the gradation value, or (2) a rotation angle for minimizing a value which is obtained by dividing the standard deviation of the gradation values of a plurality of optical images of the programmed defect obtained by changing the rotation angle, by a square root of an average gradation value obtained from the gradation values;

applying a magnetic field to the Faraday rotator such that the obtained rotation angle is achieved;

acquiring an optical image of the first pattern while the magnetic field is applied to the Faraday rotator; and detecting the existence of a defect of the first pattern using the optical image of the first pattern;

wherein the first pattern and the second pattern are a line-and-space pattern, and wherein the programmed defect comprises at least one of a pattern bridge defect in which lines are short-circuited with each other, a broken pattern defect in which the line is disconnected, and a defect caused by an edge roughness.

12. The inspection method according to claim 4, wherein the optical unit comprises a polarization beam splitter, a half-wavelength plate, a Faraday rotator, and an objective lens, further comprising:

after the focus offset value is adjusted, emitting light from the light source, reflecting the light by the polarization beamsplitter, transmitting the light through the half-wavelength plate, the Faraday rotator, the objective lens, irradiating the substrate with the light having a polarization plane of an angle except an angle within a range of an angle equal to or larger than −5 degrees and an angle equal to or smaller than 5 degrees, and a range of an angle equal to or larger than 85 degrees and an angle equal to or smaller than 95 degrees with respect to a repetitive direction of a repetitive pattern of the first pattern, transmitting the light reflected by the substrate through the objective lens, the half-wavelength plate, the Faraday rotator, and the polarization beamsplitter, acquiring an optical image of the programmed defect by causing the light to be incident to the sensor;

obtaining a gradation value in each pixel with respect to the optical image of the programmed defect, obtaining (1) a rotation angle of the polarization plane of the light rotated by the Faraday rotator for minimizing a standard deviation of the gradation value, or (2) a rotation angle for minimizing a value which is obtained by dividing the standard deviation of the gradation values of a plurality of optical images of the programmed defect obtained by changing the rotation angle, by a square root of an average gradation value obtained from the gradation values;

applying a magnetic field to the Faraday rotator such that the obtained rotation angle is achieved;

acquiring an optical image of the first pattern while the magnetic field is applied to the Faraday rotator; and detecting the existence of a defect of the first pattern using the optical image of the first pattern;

wherein the first pattern and the second pattern are a line-and-space pattern, and wherein the programmed defect comprises at least one of a pattern bridge defect in which lines are short-circuited with each other, a broken pattern defect in which the line is disconnected, and a defect caused by an edge roughness.

13. The inspection method according to claim 5, wherein the optical unit comprises a polarization beam splitter, a half-wavelength plate, a Faraday rotator, and an objective lens, further comprising:

after the focus offset value is adjusted, emitting light from the light source, reflecting the light by the polarization beamsplitter, transmitting the light through the half-wavelength plate, the Faraday rotator, the objective lens, irradiating the substrate with the light having a polarization plane of an angle except an angle within a range of an angle equal to or larger than −5 degrees and an angle equal to or smaller than 5 degrees, and a range of an angle equal to or larger than 85 degrees and an angle equal to or smaller than 95 degrees with respect to a repetitive direction of a repetitive pattern of the first pattern, transmitting the light reflected by the substrate through the objective lens, the half-wavelength plate, the Faraday rotator, and the polarization beamsplitter, acquiring an optical image of the programmed defect by causing the light to be incident to the sensor;

obtaining a gradation value in each pixel with respect to the optical image of the programmed defect, obtaining (1) a rotation angle of the polarization plane of the light rotated by the Faraday rotator for minimizing a standard deviation of the gradation value, or (2) a rotation angle for minimizing a value which is obtained by dividing the standard deviation of the gradation values of a plurality of optical images of the programmed defect obtained by changing the rotation angle, by a square root of an average gradation value obtained from the gradation values;

applying a magnetic field to the Faraday rotator such that the obtained rotation angle is achieved;

acquiring an optical image of the first pattern while the magnetic field is applied to the Faraday rotator; and detecting the existence of a defect of the first pattern using the optical image of the first pattern;

wherein the first pattern and the second pattern are a line-and-space pattern, and wherein the programmed defect comprises at least one of a pattern bridge defect in which lines are short-circuited with each other, a broken pattern defect in which the line is disconnected, and a defect caused by an edge roughness.

14. An inspection method for inspecting a substrate to detect the existence of a defect using an optical image obtained by irradiating a substrate with light emitted from a light source through an optical unit, and causing the light reflected by the substrate to be incident to a sensor through the optical unit, wherein the substrate includes a first pattern consisting of a repetitive pattern finer than the resolution limit of the optical unit, a second pattern arranged on the same plane as the first pattern, having the same direction as the first pattern, and consisting of a repetitive pattern finer than the resolution limit of the optical unit, a programmed defect disposed in the second pattern, finer than the resolution limit of the optical unit, and a third pattern arranged on the same plane as the first pattern, having a shape reflecting the direction of the first pattern, not finer than the resolution limit of the optical unit;

wherein the first pattern and the second pattern are a line-and-space pattern;

wherein the programmed defect comprises at least one of a pattern bridge defect in which lines are short-circuited with each other, a broken pattern defect in which the line is disconnected, and a defect caused by an edge roughness;

wherein the optical unit comprises a polarization beam splitter, a half-wavelength plate, a Faraday rotator, and an objective lens, and is configured to acquire an optical image of the programmed defect, after a focus offset value is adjusted, emitting light from the light source, reflecting the light by the polarization beamsplitter, transmitting the light through the half-wavelength plate, the Faraday rotator, the objective lens, irradiating the substrate with the light having a polarization plane of an angle except an angle within a range of an angle equal to or larger than −5 degrees and an angle equal to or smaller than 5 degrees, and a range of an angle equal to or larger than 85 degrees and an angle equal to or smaller than 95 degrees with respect to a repetitive direction of a repetitive pattern of the first pattern, transmitting the light reflected by the substrate through the objective lens, the half-wavelength plate, the Faraday rotator, and the polarization beamsplitter, causing the light to be incident to the sensor; the inspection method comprising:

setting a condition range of a focus offset value for adjusting the focus offset value;

setting a condition range of an angle of the Faraday rotator for adjusting an angle with respect to the repetitive direction of the repetitive pattern of the first pattern;

acquiring an optical image of the programmed defect under a plurality of conditions within the range of the condition range of a focus offset value while changing the condition of the focus offset value, and changing the condition of the angle of the Faraday rotator within the condition range of an angle of the Faraday rotator;

analyzing the plurality of optical images, and then calculating an evaluation scale by dividing a signal intensity of either the pattern bridge defect or the broken pattern defect of the programmed defect by a signal intensity of noise caused by the edge roughness;

extracting the condition of the focus offset value and the condition of an angle of the Faraday rotator for acquiring an optical image of the programmed defect using the evaluation scale, and then determining the inspection condition of the focus offset value and the inspection condition of the angle of the Faraday rotator for detecting the existence of a defect of the first pattern; and acquiring an optical image of the first pattern according to the inspection condition of the focus offset value and the inspection condition of the angle of the Faraday rotator, and then detecting the existence of a defect of the first pattern.

15. The inspection method according to claim 14, wherein the substrate comprises an alignment mark area in a scribe line area arranged in the outer periphery portion of the area in which the first pattern is disposed; and wherein the second pattern and the third pattern are disposed in any area of the scribe line area except the alignment mark area.

16. The inspection method according to claim 14,
wherein the substrate comprises an alignment mark area in a scribe line area arranged in the outer periphery portion of the area in which the first pattern is disposed;
wherein the alignment mark area includes an area comprising the second pattern, and an area in which the second pattern is not disposed, for forming the alignment mark by the difference of the contrast between the area in which the second pattern is not disposed, and the area in which the second pattern is disposed; and
wherein the third pattern also functions as the alignment mark.

17. The inspection method according to claim 14,
wherein the programmed defect comprises a plurality of defects of the same type and with different dimensions.

18. A template comprising:
an imprint surface comprising a pattern area in which a first pattern is disposed, and
a scribe line area, surrounding the first pattern;
wherein the scribe line area comprises an alignment mark area in which an alignment mark is arranged,
a second pattern and a third pattern disposed in any area of the scribe line area except the alignment mark area, and
a programmed defect disposed in the second pattern;
wherein the first pattern consists of a repetitive pattern finer than the resolution limit of an optical unit of an inspection apparatus for detecting the existence of a defect of the first pattern by acquiring an optical image of the first pattern;
wherein the second pattern has the same direction as the first pattern, and consists of a repetitive pattern finer than the resolution limit of the optical unit;
wherein the programmed defect is finer than the resolution limit of the optical unit; and
wherein the third pattern has a shape reflecting the direction of the first pattern, not finer than the resolution limit of the optical unit.

19. A template comprising:
an imprint surface comprising a pattern area in which a first pattern is disposed, and
a scribe line area, surrounding the first pattern;
wherein the scribe line area comprises an alignment mark area,
wherein the alignment mark area includes a second pattern having the same direction as the first pattern, and consists of a repetitive pattern finer than the resolution limit of an optical unit of an inspection apparatus for detecting the existence of a defect of the first pattern by acquiring an optical image of the first pattern,
a programmed defect disposed in the second pattern, finer than the resolution limit of the optical unit; and
an area in which the second pattern is not disposed, for forming the alignment mark by the difference of the contrast between the area in which the second pattern is not disposed, and the area in which the second pattern is disposed;
wherein the alignment mark has a shape reflecting the direction of the first pattern, not finer than the resolution limit of the optical unit.

* * * * *